US010471219B2

(12) United States Patent
Jones et al.

(10) Patent No.: US 10,471,219 B2
(45) Date of Patent: Nov. 12, 2019

(54) DRUG DELIVERY DEVICE WITH VARIABLE PISTON FORCE

(71) Applicant: Sanofi, Paris (FR)

(72) Inventors: Matthew Meredith Jones, Warwick (GB); William Geoffrey Arthur Marsh, Warwick (GB); Anthony Paul Morris, Warwick (GB); Samuel Keir Steel, Warwick (GB)

(73) Assignee: Sanofi, Paris (FR)

( * ) Notice: Subject to any disclaimer, the term of this patent is extended or adjusted under 35 U.S.C. 154(b) by 195 days.

(21) Appl. No.: 15/528,307

(22) PCT Filed: Nov. 24, 2015

(86) PCT No.: PCT/EP2015/077496
§ 371 (c)(1),
(2) Date: May 19, 2017

(87) PCT Pub. No.: WO2016/083370
PCT Pub. Date: Jun. 2, 2016

(65) Prior Publication Data
US 2017/0340835 A1     Nov. 30, 2017

(30) Foreign Application Priority Data
Nov. 24, 2014   (EP) .................................... 14306862

(51) Int. Cl.
*A61M 5/31* (2006.01)
*A61M 5/315* (2006.01)
*A61M 5/20* (2006.01)

(52) U.S. Cl.
CPC .......... *A61M 5/31583* (2013.01); *A61M 5/20* (2013.01); *A61M 5/2046* (2013.01);
(Continued)

(58) Field of Classification Search
CPC ............ A61M 5/20; A61M 2005/2086; A61M 5/31565; A61M 5/3159; A61M 5/31593
See application file for complete search history.

(56) References Cited

U.S. PATENT DOCUMENTS

2005/0261634 A1* 11/2005 Karlsson ................. A61M 5/20
604/197
2006/0276753 A1* 12/2006 Kronestedt ............. A61M 5/20
604/186
(Continued)

FOREIGN PATENT DOCUMENTS

EP        1 728 529        12/2006
WO    WO 2010/053569      5/2010
(Continued)

OTHER PUBLICATIONS

International Search Report and Written Opinion in International Application No. PCT/EP2015/077496, dated Jan. 26, 2016, 9 pages.
(Continued)

*Primary Examiner* — William R Carpenter
(74) *Attorney, Agent, or Firm* — Fish & Richardson P.C.

(57) ABSTRACT

The present disclosure relates to a drug delivery device, comprising a housing, a cartridge, the cartridge containing a drug in a quantity sufficient for a plurality of doses of the drug, a bung, the bung being movably retained within the cartridge to dispense a dose of the drug from the cartridge upon movement of the bung with respect to the cartridge, and a drive mechanism, the drive mechanism being operable to transfer a driving force to the bung to dispense the dose of the drug from the cartridge. The drug delivery device is configured such that the maximal driving force which is transferrable to the bung via the drive mechanism varies and is adjusted to the current position of the bung within the cartridge.

13 Claims, 9 Drawing Sheets

(52) U.S. Cl.
    CPC .... *A61M 5/31515* (2013.01); *A61M 5/31545* (2013.01); *A61M 5/31553* (2013.01); *A61M 5/31558* (2013.01); *A61M 2005/3126* (2013.01); *A61M 2205/581* (2013.01); *A61M 2205/582* (2013.01)

(56)            References Cited

U.S. PATENT DOCUMENTS

| | | | |
|---|---|---|---|
| 2011/0092905 A1* | 4/2011 | Cowe | A61M 5/20 604/135 |
| 2012/0209208 A1* | 8/2012 | Stefanski | A61M 5/20 604/189 |
| 2013/0197442 A1* | 8/2013 | Cowe | A61M 5/2033 604/131 |
| 2016/0235926 A1* | 8/2016 | Blancke | A61M 5/24 |
| 2016/0279337 A1* | 9/2016 | Blancke | A61M 5/3155 |

FOREIGN PATENT DOCUMENTS

| | | |
|---|---|---|
| WO | WO 2011/101377 | 8/2011 |
| WO | WO 2014/033197 | 3/2014 |

OTHER PUBLICATIONS

International Preliminary Report on Patentability in International Application No. PCT/EP2015/077496, dated May 30, 2017, 7 pages.

\* cited by examiner

Figure 9
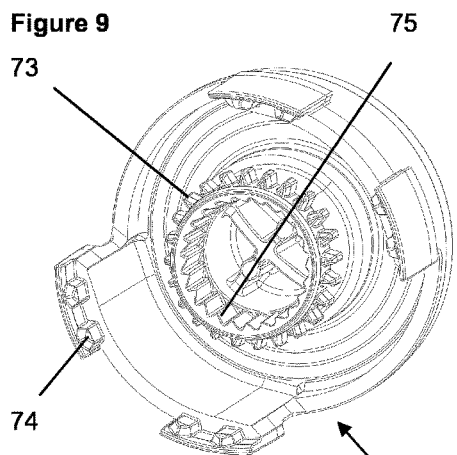
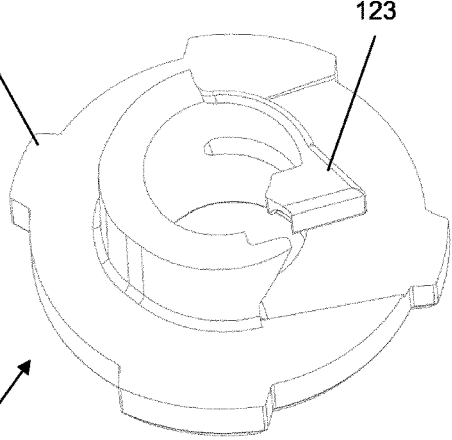
Figure 10
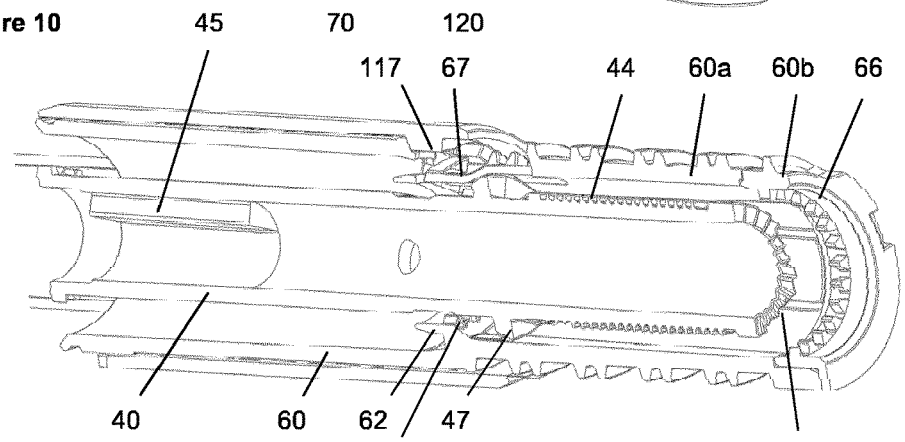
Figure 11a
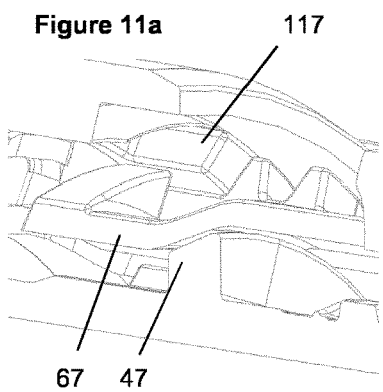
Figure 11b
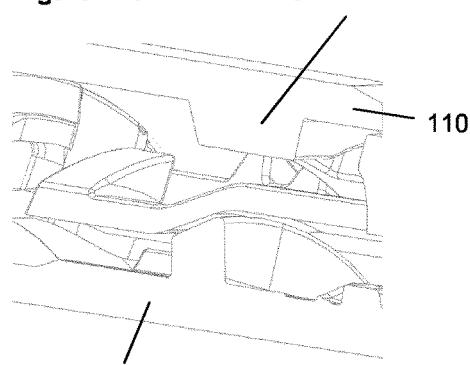
Figure 11c
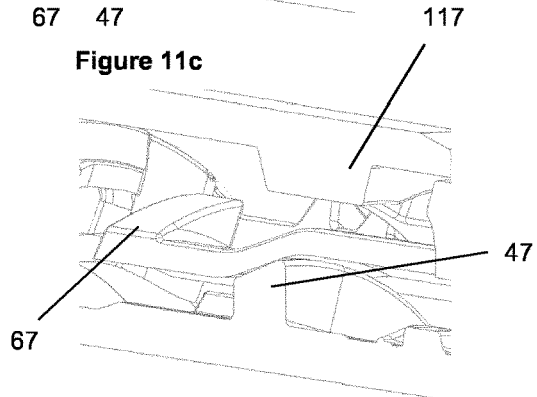

Figure 21
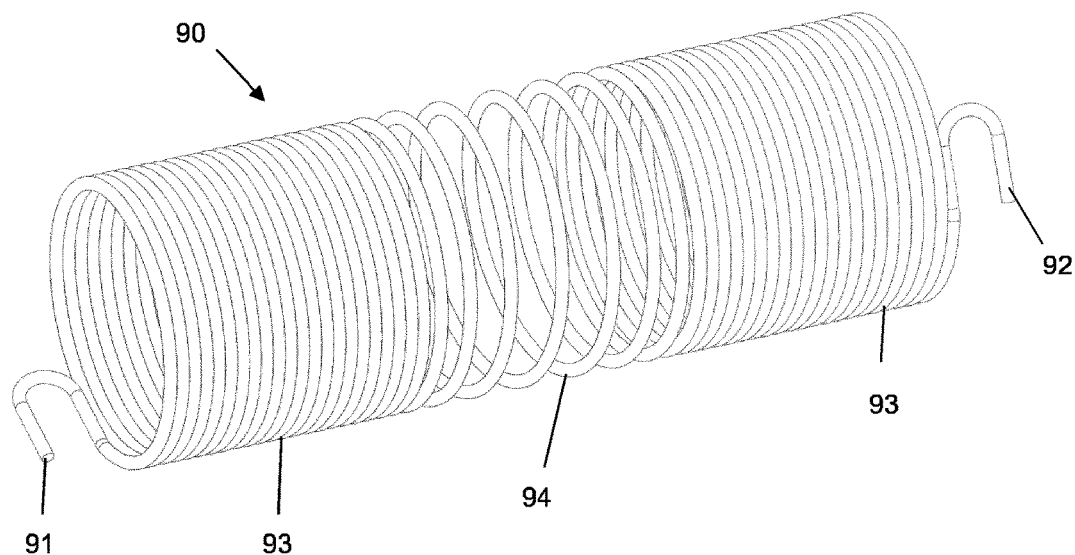
Figure 22a   Figure 22b   Figure 22c
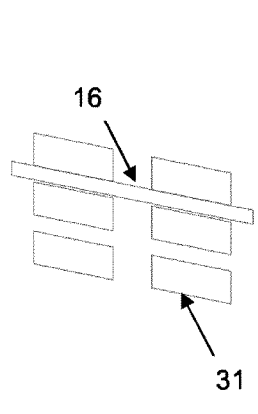
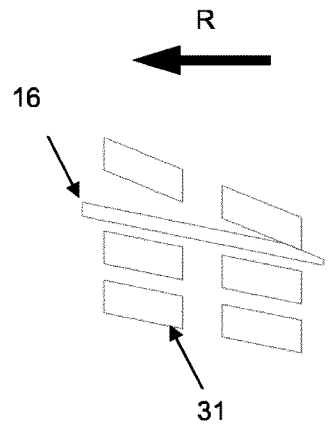
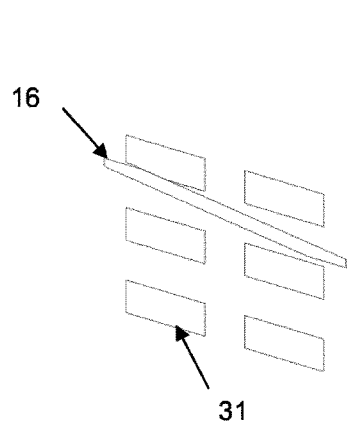

DRUG DELIVERY DEVICE WITH VARIABLE PISTON FORCE

CROSS-REFERENCE TO RELATED APPLICATIONS

This application is a U.S. national stage application under 35 USC § 371 of International Application No. PCT/EP2015/077496, filed on Nov. 24, 2015, which claims priority to European Patent Application No. 14306862.5, filed on Nov. 24, 2014, the entire contents of which are incorporated herein by reference.

TECHNICAL FIELD

The present disclosure is generally directed to a drug delivery device, particularly to a drug delivery device which is suitable for selecting and dispensing a number of, preferably user variable, doses of a drug or medicament.

BACKGROUND

Drug delivery devices, such as pen type drug delivery devices, have application where regular injection by persons without formal medical training occurs. This may be increasingly common among patients having diabetes where self-treatment enables such patients to conduct effective management of their disease. In practice, such a drug delivery device allows a user to individually select and dispense a number of user variable doses of a medicament. The present disclosure is, in general not limited to variable dose devices, but would also be applicable for so called fixed dose devices which only allow dispensing of a predefined dose without the possibility for the user to increase or decrease the set dose.

There are basically two types of drug delivery devices: resettable devices (i.e., reusable) and non-resettable (i.e., disposable) devices. For example, disposable pen delivery devices are supplied as self-contained devices. Such self-contained devices do not have removable pre-filled cartridges. Rather, the pre-filled cartridges may not be removed and replaced from these devices without destroying the device itself. Consequently, such disposable devices need not have a resettable dose setting mechanism. The present disclosure is applicable for both types of devices, i.e. for disposable devices as well as for reusable devices.

Drug delivery devices, particularly pen delivery devices (so named because they often resemble an enlarged fountain pen), generally comprise three primary elements: a cartridge section that includes a cartridge often contained within a housing or holder; a needle assembly connected to one end of the cartridge section; and a dosing section connected to the other end of the cartridge section. A cartridge (often referred to as an ampoule) typically includes a reservoir that is filled with a medication or drug (e.g., insulin). A movable, e.g. rubber type, bung or stopper is typically located at one end of the cartridge reservoir, and a top having a pierceable, e.g. rubber, seal or septum is typically located at the other, often necked-down, end. A crimped annular metal band is typically used to hold the rubber seal in place. While the cartridge housing may be typically made of plastic, cartridge reservoirs have historically been made of glass.

The needle assembly is typically a replaceable double-ended needle assembly. Before an injection, a replaceable double-ended needle assembly is attached to one end of the cartridge assembly, a dose is set, and then the set dose is administered. Such removable needle assemblies may be threaded onto, or pushed (i.e., snapped) onto the pierceable seal end of the cartridge assembly.

The dosing section or dose setting mechanism is typically the portion of the pen device that is used to set (select) a dose. During an injection, a spindle or piston rod contained within the dose setting mechanism, often also called drive mechanism, presses against the bung or stopper of the cartridge. This force causes the drug contained within the cartridge to be injected through an attached needle assembly. After an injection, as generally recommended by most drug delivery device and/or needle assembly manufacturers and suppliers, the needle assembly is removed and discarded.

A further differentiation of drug delivery device types refers to the drive mechanism: There are devices which are manually driven, e.g. by a user applying a force to an injection button, devices which are driven by a spring or the like and devices which combine these two concepts, i.e. spring assisted devices which still require a user to exert an injection force. The spring-type devices involve springs which are preloaded and springs which are loaded by the user during dose selecting. Some stored-energy devices use a combination of spring preload and additional energy provided by the user, for example during dose setting.

WO 2014/033197 A1 describes a manually driven drug delivery device with a housing, a dose setting button operable to set a dose by rotation relative to the housing, a number sleeve arranged within the housing such that at least a portion of the number sleeve is visible through a first aperture in the housing, a piston rod coupled to the housing and to a driver such that rotation of the driver relative to the housing causes the piston rod to translate relative to the housing, and a clutch mechanism releasably coupling the number sleeve and the driver. The piston rod is in threaded engagement with an inner housing and in threaded engagement with the driver such that the piston rod advances by a fixed displacement for each revolution of the drive sleeve.

SUMMARY

One aspect of the present disclosure relates to a drug delivery device. In an embodiment, the drug delivery device comprises a housing. The housing, which is preferably an exterior housing of the device, may be provided to house interior parts of the drug delivery device, such as a cartridge and/or one or more parts of a drive mechanism of the device, like a piston rod, for example. The housing may have a proximal end and a distal end. The distal end of the housing or any other part of the drug delivery device may be that end which faces, or should be arranged to face, the dispensing end of the device. The dispensing end of the device is usually that end, where the needle or needle assembly is mounted. The proximal end of the housing or of a component of the device is preferably that end which faces away or shall be arranged to face away from the dispensing end of the device. The housing may be of unitary structure or may be a multipart housing. For example, the housing may comprise a cartridge holder and a body, the cartridge holder retaining a cartridge and the body retaining one or more parts of a drive mechanism of the device. Body and cartridge holder are preferably secured to one another.

In an embodiment, the drug delivery device comprises a cartridge. The cartridge may contain the drug or medicament, preferably in a quantity sufficient for a plurality of doses of the drug or medicament, which should be delivered by the device. The drug may be a liquid drug.

The term "drug" or "medicament", as used herein, preferably means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;

or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2) 25, Asp28] Exendin-4(S1-39)-(Lys)6-NH2, H-Asn-(Glu)5-des Pro36, Pro37, Pro38 [Met(O)14, Trp (O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra-low molecular weight heparin or a derivative thereof, or a sulphated, e.g. a poly-sulphated form of the above-mentioned polysaccharides, and/or a pharmaceutically acceptable salt thereof An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two βsheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three on the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv). Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2) (R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

In an embodiment, the drug delivery device comprises a bung. The bung is preferably movably retained within the cartridge. Expediently, the bung is movable to dispense a dose of the drug from the cartridge upon movement of the bung with respect to the cartridge, particularly in the distal direction. The bung may sealingly contact one or more inner walls of the cartridge, preferably in order to seal the proximal end of the cartridge such that drug cannot leave the cartridge via its proximal end. For dispensing drug from the cartridge the bung may be moved towards an outlet of the cartridge, which is positioned at the distal end of the cartridge, and dispense drug from the cartridge. Expediently, for dispensing drug from the cartridge, fluid communication is established between the interior of the cartridge and the outside, for example by a needle piercing the seal or septum of the cartridge. The distance which the bung is displaced to dispense the dose of drug from the cartridge may correspond to the size of the dose which was, for example, previously set by the user of the device.

In an embodiment, the drug delivery device comprises a drive mechanism. The drive mechanism is expediently operable or operated to transfer a driving or dispensing force to the bung, particularly in order to dispense a drug, such as the previously set dose of drug, from the cartridge. The drive mechanism may be designed to transfer a maximal driving force to the bung, e.g. the maximal force transferred to the bung during the dispensing action for dispensing a single dose of drug from the cartridge. The maximal driving force may be defined by the design of the drive mechanism. For example, if the drive mechanism operates using an energy storage means comprised by the device the maximal driving force may be the maximal force that can be generated by the energy stored in the energy storage means when the energy is released in a dispensing action. Additionally or alternatively, particularly if the drive mechanism requires a user exerted force for a dispensing action—either for providing the whole driving force which is necessary for the particular dispensing action or only a part of that force—the device may comprise a force limiting mechanism which limits the force transferrable to the bung to the maximal driving force which is still sufficient to move the bung relative to the cartridge and dispense drug from the cartridge. The maximal driving force may be the maximal force transferred to the bung during the dispensing of a single dose of the drug, for example in case the driving force varies over the duration of the dispensing action for dispensing the dose.

In an embodiment, the drug delivery device, particularly the drive mechanism, is configured such that the maximal driving force which is transferred to or can be transferred to the bung via the drive mechanism varies, preferably between different doses of drug which are delivered from the device.

In an embodiment, the maximal driving force which is transferred to or transferrable to the bung via the drive mechanism, depends on the filling level or filling status, particularly the current filling level or filling status of the cartridge. Consequently, the maximal driving force may vary dependent on the current filling level of the cartridge.

In an embodiment, the maximal driving force which is transferred to or transferrable to the bung via the drive mechanism is adjusted to the current position of the bung within the cartridge. Consequently, the maximal driving force may vary dependent on the current position of the bung within the cartridge. Preferably, the maximal driving force is adjusted to a stiction force of the bung with respect to the cartridge in the current position of the bung. The stiction force may be that force which has to be overcome to move the bung relative to the cartridge. The stiction force may be that force which has to be overcome to get the bung to move with respect to the cartridge starting from a resting bung. The stiction force may act, at least partly, between the bung and the cartridge, particularly the inner wall thereof In the case of a new cartridge, e.g. a cartridge which has the same filling level or filling status as provided originally from the manufacturer, where no drug has yet been dispensed from the cartridge, the force required to move the bung relative to the cartridge in order to dispense the drug from the cartridge may be different from the force required to move the bung when the drug has already been dispensed from the cartridge. This may be due to an increase in stiction between bung and cartridge during storage of the cartridge, e.g. before the user is provided with the device or even before the cartridge is assembled with the remainder of the components of the device to form the device. Once the initial stiction force has been overcome, the subsequently acting stiction forces between cartridge and bung when the bung rests relative to the cartridge are usually less than the initial stiction force. Thus, a lower force is sufficient to get the bung to move relative to the cartridge.

Preferably, the drug delivery device is operable in two modes of operation, an initial mode of operation and a subsequent mode of operation. If the maximal driving force is adjusted to the stiction force in the current bung position, in the initial mode of operation, the drive mechanism may be designed to transfer an initial maximal driving force to the bung, which is greater than the initial stiction force. In the subsequent mode of operation, when the initial stiction force has been overcome, the drive mechanism may be designed to transfer a subsequent maximal driving force to the bung which is less than the initial maximal driving force but greater than the stiction force in the current position of the bung within the cartridge. Once the device is no longer in the initial mode of operation, the maximal driving force transferred to or transferrable to the bung by the drive mechanism is expediently always less than the initial maximal driving force. Thus, the device may be configured to provide an increased maximal driving force only in the initial mode of operation.

Accordingly, the driving forces acting in the device can be adjusted to the specific needs without excessive force being generated in the device, which are not needed when the initial stiction force has been overcome and the first drug has already been dispensed from the device.

The respective maximal driving force in the respective mode of operation is expediently greater but not to a too great extent than the stiction force in the current position of the bung.

In other words, the drug delivery device may be configured such that the maximal driving force, which can be transferred to the bung by the drive mechanism, is greater for a new cartridge than for a cartridge from which drug has already been dispensed. The maximal driving force may have a first value for a new cartridge which is greater than a second value for a cartridge which is already in use, the second value preferably being smaller than the first value for every dose subsequent to that dose when the maximal driving force has been lowered from the first value to the second value, e.g. after the first, second or third dose has been dispensed.

In an embodiment, the bung is displaceable from an initial position, preferably when all of the drug is still within the cartridge, e.g. when the cartridge is new, with respect to the cartridge via an intermediate position, preferably when the cartridge is partially emptied, to an end position, preferably when no more drug can be dispensed from the drug delivery device, e.g. when no or not enough drug is left in the cartridge or further operation of the drive mechanism is prevented after the last dose, for which the mechanism was designed, has been delivered, such as by a locking mechanism. Expediently, the maximal driving force is greater when the bung is in the initial position and/or between the initial position and the intermediate position, than when the bung is in the intermediate position and/or between the intermediate position and the end position. The intermediate position of the bung may have been reached, for example, after the first, the second or the third dose has been dispensed from the device. Before the intermediate position is reached, the maximal driving force may be greater than the maximal driving force which is transferred or transferrable to the bung on the whole way from the intermediate position to the end position. The intermediate position may be that position of the bung, when the current stiction force is significantly less than the initial stiction force. In the intermediate position, the current stiction force may be 70% or less, 60% or less, or even 50% or less than the initial stiction force in the initial position of the bung.

In an embodiment, when the bung is in its initial position, e.g. when all of the drug is still within the cartridge, the maximal driving force is greater than the stiction force which has to be overcome to move the bung with respect to the cartridge. Preferably, the maximal driving force is sufficient to move the bung with respect to the cartridge away from the initial position, particularly taking into account the higher initial stiction force. When the bung is in the intermediate position, the maximal driving force, which is preferably sufficient to displace the bung with respect to the cartridge to dispense drug from the cartridge, is expediently less than the force required to move the bung away from the initial position but greater than a stiction force of the bung in the intermediate position. In the intermediate position, the maximal driving force may be less than the stiction force in the initial position of the bung.

In other words, the drug delivery device is configured such that when the bung is in its initial position, the maximal driving force is greater than the maximal driving force when the bung has already been displaced away from the initial position.

In an embodiment, the maximal driving force varies between two subsequent doses. The maximal driving force may be greater for one of the doses, e.g. the first dose, which is dispensed from the cartridge than for a subsequent dose, preferably for any subsequent dose, which is dispensed from the cartridge.

In an embodiment, the drug delivery device comprises an energy storage member, for example a spring. The energy storage member is expediently adapted to store energy which, when released, provides at least a fraction of the driving force, such as only a fraction of the driving force, or the whole driving force. Accordingly, the drug delivery device may be an automatic drug delivery device where the force required to dispense drug from the device is provided by the energy storage member, preferably only by the energy storage member, particularly when the bung travels from the intermediate position towards the end position. On its way from the initial position to the intermediate position the drive mechanism may be configured to assist the energy storage member in order to provide an initially increased driving force. This is disclosed in more detail below. The energy storage member may be a mechanical energy storage member. The energy storage member may be a torsion spring. Torsion springs are particularly suitable to reliably provide driving forces in drug delivery devices. The energy storage member is expediently part of the drive mechanism.

In an embodiment, the drug delivery device comprises a dose setting member which is operable by the user to set the dose. For setting the dose, the user may for example rotate the dose setting member relative to the housing with or without concurrent axial movement with respect to the housing. The energy may be stored within the energy storage member by the user when operating the dose setting member to set the dose which is preferably subsequently dispensed from the device. In the case of a torsion spring, torque may be required by the user to store the energy within the energy storage member. During dose delivery, it is preferred that no user-exerted force is necessary to assist the dispensing action. This is particularly user-friendly.

In an embodiment, the drug delivery device is an automatic dispensing device, preferably where no user-exerted force is transferred to the bung to dispense the drug from the cartridge during dispensing of the drug or during a dispensing action. Rather, the energy required for the force may be already stored in the device, such as in the energy storage member. The energy may have been stored in the energy storage member before or during assembling of the device or the user may have to exert a force during dose setting to store the energy necessary for the subsequent dispensing of the dose in the energy storage member.

In an embodiment, the drug delivery device is configured such that the maximal force transferable to the bung and originating from the energy released from the energy storage member is only a fraction of the driving force required to move the bung from the initial position towards the intermediate position. In this case, it is preferred that supplemental energy—either by a member within the device or by the user—is provided, in addition to the energy stored in the energy storage member to enable provision of the driving force required to move the bung.

In an embodiment, the drug delivery device comprises a supplemental storage member within which supplemental energy is stored. The supplemental energy is expediently provided to, when released, provide energy, preferably in addition to that provided by the energy storage member, for a supplemental force to move the bung from the initial position towards the intermediate position. The energy stored in the supplemental storage member may be less than the energy required to move the bung away from the initial position. Consequently, a fraction of the driving force required to move the bung away from the initial position may be provided by the supplemental storage member and another fraction, preferably the remaining fraction of this driving force, may be provided by the energy storage member. This is particularly suitable, if the energy stored in the energy storage member is not sufficient to move the bung away from the initial position.

The supplemental storage member may be configured to assist, preferably to only temporarily assist, the energy storage member in providing the driving force. The supplemental storage member may be configured to assist the energy storage member in providing the driving force at the beginning, preferably only at the beginning, of the emptying of the cartridge, i.e. when the bung is moved from the initial position to the intermediate position. Once the intermediate position has been reached, the supplemental energy is expediently no longer provided as only a lower driving force is required to move the bung in the intermediate position. The supplemental energy may be stored in the supplemental storage member when the device is assembled. Preferably, the user has no influence on the energy stored in the storage member except that he may release the energy when operating the drug delivery device. The supplemental storage member can preferably not be reloaded once all of the energy has been released from the supplemental storage member.

In an embodiment, the supplemental storage member is a mechanical storage member. The supplemental storage member may be or may comprise a spring. The spring may be pre-biased, such as during assembly of the device. Preferably, the spring may be not user-loadable or biasable during operation of the drug delivery device. The supplemental storage member may, for example, be a compression spring, a leaf spring, or a washer spring. Alternatively or additionally, the supplemental storage member may be or may comprise a cartridge or reservoir which is filled with gas, preferably pressurized gas. When the pressurized gas expands, e.g. once the interior of the cartridge or reservoir is in fluid communication, for example because an outer shell of the cartridge is destroyed during the initial operation of the drive mechanism, with the exterior, supplemental energy can be transferred to the bung in order to increase the driving force to displace the bung from its initial position towards the intermediate position.

In an embodiment, the drive mechanism comprises a piston rod. The piston rod may be configured to transfer the driving force to the bung. The piston rod may be coupleable to a dose dispensing member of the device, for example to a button, immediately or via further components of the drive mechanism. Actuation of the dose dispensing member by the user may initiate the dispensing action for a previously set dose. By means of the piston rod, movement of the bung with respect to the cartridge may be driven during the dispensing action. For contacting the bung of the cartridge, a bearing may be attached to the piston rod, particularly to a distal end thereof. The piston rod may be rotatably connected to the bearing such that the piston rod may rotate relative to the bearing. Alternatively, a bearing surface may be provided by a, preferably unitary, piston rod. The piston rod may be configured to rotate relative to the housing. In this case, the piston rod is preferably coupled to the housing via a threaded interface. Consequently, rotation of the piston rod is converted into axial displacement of the piston rod with respect to the housing. Alternatively, the piston rod is threadedly engaged with a nut and is prevented from rotating with respect to the housing where the nut is allowed to rotate relative to the housing, thereby displacing the piston rod with respect to the housing.

In an embodiment, the piston rod is displaceable away from an initial position, preferably towards an end position of the piston rod, as the bung is displaced relative to the cartridge. In the initial position of the piston rod, the bung is expediently also in its initial position.

In an embodiment, in the initial position of the bung and/or of the piston rod, the piston rod is mechanically decoupled from the bung. That is to say, in the initial position, there may be a gap between piston rod and bung and/or between bung and bearing. Alternatively in the initial position of the bung and/or of the piston rod the piston rod is mechanically coupled to the bung. In this case, the piston rod, or the bearing attached to the piston rod, may be in mechanical contact with the bung in the initial position. Expediently, in this case the piston rod or the bearing and the bung abut.

In an embodiment, the supplemental storage member mechanically cooperates with the piston rod and is arranged to assist movement of the piston rod to drive movement of the bung.

In an embodiment, the supplemental storage member acts, e.g. directly or indirectly, on the piston rod.

As the energy stored in the supplemental storage member is preferably less than the energy required to move the bung away from the initial position, i.e. the maximum force exertable by the energy stored in the supplemental storage member is preferably less than the initial stiction force, it can be avoided that medicament or a drug is dispensed from the cartridge due to a pre-bias of the bung when the needle is attached to the drug delivery device and provides fluid communication between the interior of the cartridge and the outside, even if the bung and the piston rod are mechanically coupled in the initial position.

In an embodiment, the supplemental storage member is arranged to bias or biases the piston rod. The supplemental storage member may bias the piston rod in the distal direction and/or away from the initial position of the piston rod. The supplemental storage member may bias the piston rod in the direction towards the bung, expediently in an initial position of the piston rod.

In an embodiment, the energy stored in the supplemental storage member is less than the energy required to move the piston rod away from the initial position of the piston rod. The piston rod may remain in the initial position, even though the piston rod is mechanically decoupled from the bung and even though the supplemental storage member exerts a force on the piston rod in the distal direction. The biasing force exerted by the supplemental storage member may, in this case, be lower than the internal static friction forces in the drive mechanism in the initial position of the piston rod.

In an embodiment, the supplemental storage member acts on the piston rod or biases the piston rod only temporarily. Accordingly, there is a certain point in time during the travel of the piston rod towards its end position from which point onwards the supplemental storage member no longer acts on the piston rod. When the supplemental storage member no longer exerts a force on the piston rod, the bung may be in the intermediate position.

In an embodiment, the supplemental storage member acts on the piston rod via the bearing. Particularly, the supplemental storage member may be retained between an element fixed, preferably axially and rotationally, to the housing and the bearing or between the housing and the bearing. Consequently, in the initial position of the piston rod there may be a state of tension between piston rod and bearing. Particularly, a distal surface of the bearing and a proximal surface of the piston rod may be in contact with each other in the initial position of the piston rod. When the piston rod is displaced from the initial position and moves the bung away from its initial position, it is preferred that a proximal surface of the bearing and a distal surface of the piston rod abut before the bung moves. Thereby, a state of compression may be established between piston rod and bearing before the first dose is delivered. The state of compression may be established continuously after the bung has been displaced away from its initial position. Thus, the piston rod and bearing may be in the state of compression all the time when drug has already been dispensed form the device, preferably also when there is no movement of the piston rod. A constant compression state is more reliable when dispensing doses than varying between a tension state and a compression state. A switch from the state of tension to the state of compression before the first amount of drug is dispensed from the cartridge may be achieved by choosing the supplemental storage member to have an energy stored therein which is less than the one required to move the bung away from the initial position.

In an embodiment, the supplemental storage member, e.g. the cartridge with the pressurized gas, is arranged between the piston rod or bearing and the bung.

In an embodiment, the piston rod comprises a thread, e.g. a helical thread. The piston rod may be coupled to the housing via the thread. The thread may have a variable pitch and/or a variable lead. The thread is expediently configured such that the maximal dispensing force which is transferrable to the bung varies, e.g. even if the same torque is exerted by the energy storage member. Particularly, the energy storage member may, in this case, be configured to supply the whole energy required to move the bung with respect to the cartridge. The supplemental storage member may be, but does not need to be, dispensed with in this case. For example, if the thread has a section with a finer pitch or lower lead, a given torque acting on the piston rod results in less axial displacement and a correspondingly increased force acting on the bung than in a section with coarser pitch or higher lead.

In an embodiment, the thread has a distal section, particularly a distal end section, facing a distal end of the piston rod and a proximal section, the proximal section being arranged further away from the distal end of the piston rod than the distal section. In the distal section the pitch of the thread and/or the lead of the thread is preferably less than the pitch of the thread and/or the lead of the thread in the proximal section. Accordingly, in the distal section the pitch/lead may be less than the pitch/lead in the proximal section. Particularly, in the distal section the thread may be more finely pitched than in the proximal section. Preferably, the pitch/lead in the respective section is constant and changes only in an intermediate section arranged between the distal section and the proximal section. There may be only one intermediate section. Consequently, as the distal section is the one which governs displacement of the piston rod away from the initial position and also the initial movement of the bung, the distal section is designed to increase the driving force in the initial bung position.

By means of the according thread design, it can be achieved that, provided a given torque provided by the energy storage member is used to drive the piston rod distally, there is less axial displacement when the distal section is used to drive movement of the piston rod on account of its finer pitch or lower lead which results in a higher force being transferred to the bung, this force being expediently greater than the stiction force in the initial position of the bung.

In an embodiment, the piston rod is coupled to the housing via a threaded interface with constant pitch. In this case, the thread of the piston rod may have a constant pitch.

In an embodiment, the piston rod is coupled to the housing via a first threaded interface. The first threaded interface may have a constant pitch and/or lead. The first threaded interface may be formed by means of the thread of the piston rod described above, for example in cooperation with an engagement member which is axially fixed relative to the housing. The pitch of the thread of the piston rod which threadedly couples the piston rod to the housing may be constant. The piston rod may be coupled to a further component of the drug delivery device via a second threaded interface. The first and second threaded interfaces may have different pitches and/or leads. The second threaded interface and the first threaded interface may be adjusted with respect to each other, in particular with respect to the pitches and/or leads, such that, when the second threaded interface is active, for example if the further component threadedly interacts with the piston rod via the second threaded interface, the force acting on the bung is increased when the first threaded interface is also active. The pitch and/or lead of the second threaded interface may be smaller than the pitch and/or lead of the first threaded interface. The second threaded interface may be active only temporarily, for example in order to provide only an increased initial driving force in order to displace the bung away from its initial position. The first threaded interface may be active continuously. The second threaded interface may be formed by a further thread of the piston rod, e.g. a helical thread. The further thread may have a smaller pitch and/or a smaller lead than the thread which couples the piston rod to the housing. The further component which is coupled to the piston rod via the second threaded interface may be the bearing described above.

In a particularly advantageous embodiment, a drug delivery device is provided, comprising a housing, a cartridge, the cartridge containing a drug in a quantity sufficient for a plurality of doses of the drug, a bung, the bung being movably retained within the cartridge to dispense a dose of the drug from the cartridge upon movement of the bung with respect to the cartridge, a drive mechanism, the drive mechanism being operable to transfer a driving force to the bung to dispense the dose of the drug from the cartridge, wherein the drug delivery device is configured such that the maximal driving force which is transferrable to the bung via the drive mechanism varies and is adjusted to the current position of the bung within the cartridge.

This embodiment has a number of advantages which will be readily apparent from the description above and below.

Of course, features described in conjunction with different embodiments, aspects, etc. herein above and below can be combined with one another.

Further features, advantages and advantageous refinements of the present disclosure become apparent from the following description of the exemplary embodiments in conjunction with the drawings. The description of the exemplary embodiments does not limit the scope of the present disclosure.

BRIEF DESCRIPTION OF THE FIGURES

FIG. 9 shows an interface between the clutch plate and the button of the device of FIG. 1;

FIG. 10 shows in a sectional view the components of an end of dose clicker of the device of FIG. 1;

FIGS. 11a-c show in enlarged views the sequence of generating a click at the end of dose dispensing of the device of FIG. 1;

FIG. 21 shows the torsion spring of the device of FIG. 1;

FIGS. 22a-c show different embodiments of the threads between the piston rod and the housing of the device of FIG. 1;

Identical features, features of the same kind and/or identically acting features may be provided with the same reference numerals throughout the figures.

DETAILED DESCRIPTION

Figure 1:
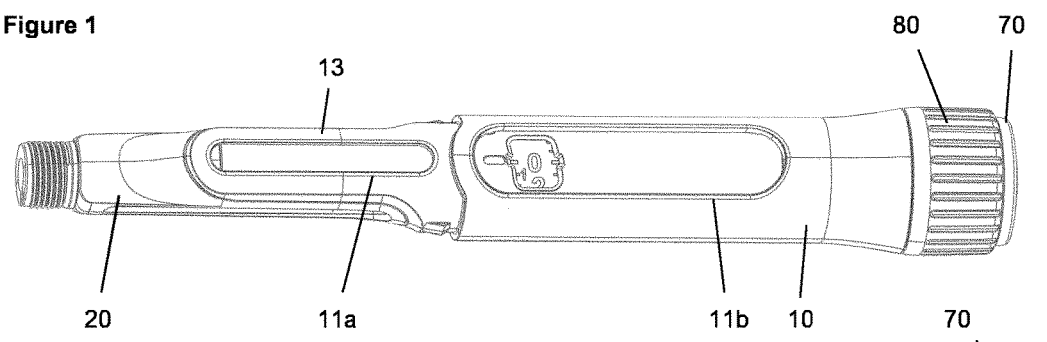
FIG. 1 shows a top view of an exemplary embodiment of a drug delivery device of the present disclosure in a minimum dose position.
Figure 2:
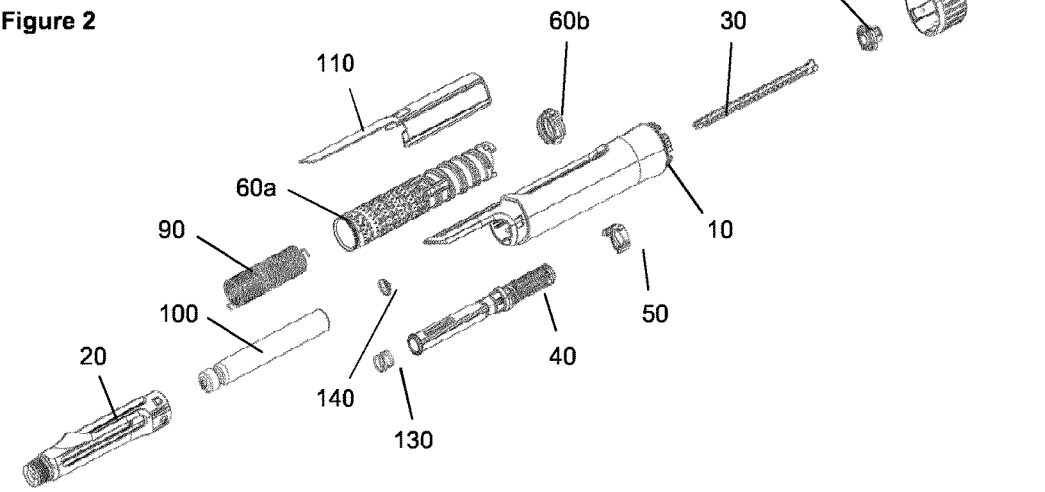
FIG. 2 shows an exploded view of the components of the device of FIG. 1.

FIG. 1 shows a drug delivery device in the form of an injection pen. The device has a distal end (left end in FIG. 1) and a proximal end (right end in FIG. 1). The component parts of the drug delivery device are shown in FIG. 2. The drug delivery device comprises a body or housing 10, a cartridge holder 20, a lead screw or piston rod 30, a drive sleeve 40, a nut 50, a dose indicator or number sleeve 60, a button 70, a dial grip or dose selector 80, a torsion spring 90, a cartridge 100, a gauge element 110, a clutch plate 120, a clutch spring 130 and a bearing 140. A needle arrangement (not explicitly shown) with a needle hub and a needle cover may be provided as additional components, which can be exchanged as explained above. The device comprises a principal axis 1 (see FIG. 3). All components are preferably located concentrically about the common principal axis I of the mechanism.

The housing 10 or body is a generally tubular element having a proximal end with an enlarged diameter. The housing 10 provides location for the liquid medication cartridge 100 and cartridge holder 20, windows 11a, 11b for viewing the dose number on the number sleeve 60 and the gauge element 110, and a feature on its external surface, e.g. a circumferential groove, to axially retain the dose selector 80. A flange-like or cylindrical inner wall 12 comprises an inner thread engaging the piston rod 30. The housing 10 further has at least one internal, axially orientated slot or the like for axially guiding the gauge element 110. In the embodiment shown in the Figures, the distal end is provided with an axially extending strip 13 partly overlapping cartridge holder 20. The Figures depict the housing 10 as a single housing component. However, the housing 10 could comprise two or more housing components which may be permanently attached to each other during assembly of the device.

The cartridge holder 20 is located at the distal side of housing 10 and permanently attached thereto. The cartridge holder may be a transparent or translucent component which is tubular to receive cartridge 100. The distal end of cartridge holder 20 may be provided with means for attaching a needle arrangement. A removable cap (not shown) may be provided to fit over the cartridge holder 20 and may be retained via clip features on the housing 10.

Figure 8:
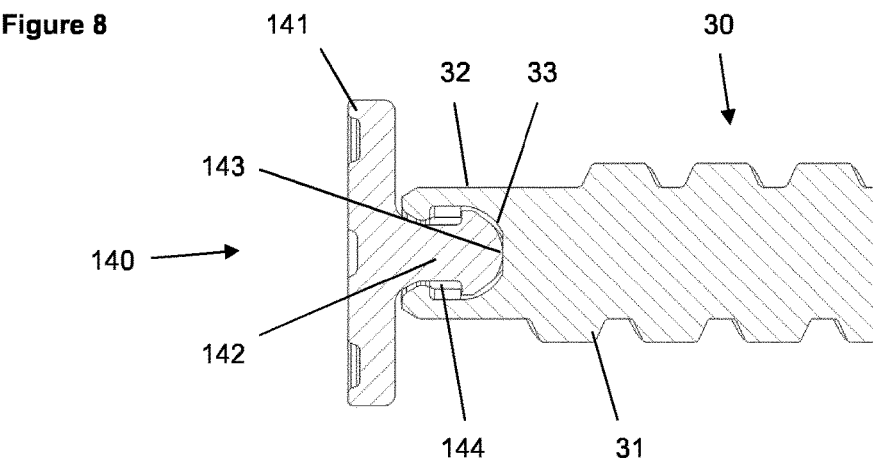
FIG. 8 shows an interface between a piston rod and a bearing of the device of FIG. 1.

The piston rod 30 is rotationally constrained to the drive sleeve 40 via a splined interface. When rotated, the piston rod 30 is forced to move axially relative to the drive sleeve 40, through its threaded interface with the inner wall 12 of housing 10. The lead screw 30 is an elongate member with an outer thread 31 (FIG. 3) engaging the corresponding thread of the inner wall 12 of housing 10. The thread 31 may have a large lead-in, for example a wedge shape form, at its distal end to engage a corresponding housing thread form on the first rotation. The interface comprises at least one longitudinal groove or track and a corresponding protrusion or spline 45 of the driver or drive sleeve 40. At its distal end, the lead screw 30 is provided with an interface for clip attachment of the bearing 140. In the present embodiment, this interface comprises two clip arms 32 extending in the distal direction defining an insertion space between them for insertion of a bearing 140 interface. As an alternative, the interface may comprise only one single clip arm extending more than 180° about the longitudinal axis, or may comprise one or several clip arms 32. The clip arm(s) 32 may have a bent form with a recessed clip portion as shown in FIG. 8. Preferably, the clip arm(s) form a cylindrical outer face having a diameter equal to or smaller than the outer diameter of the lead screw 30 at the base of the groove (flute base) of the outer thread 31. A concave contact surface 33 is provided between the clip arms 32 for abutment of a corresponding portion of bearing 140.

The drive sleeve 40 is a hollow member surrounding the lead screw 30 and arranged within number sleeve 60. It extends from an interface with the clutch plate 120 to the contact with the clutch spring 130. The drive sleeve 40 is axially movable relative to the housing 10, the piston rod 30 and the number sleeve 60 in the distal direction against the bias of clutch spring 130 and in the opposite proximal direction under the bias of clutch spring 130.

Figure 18:
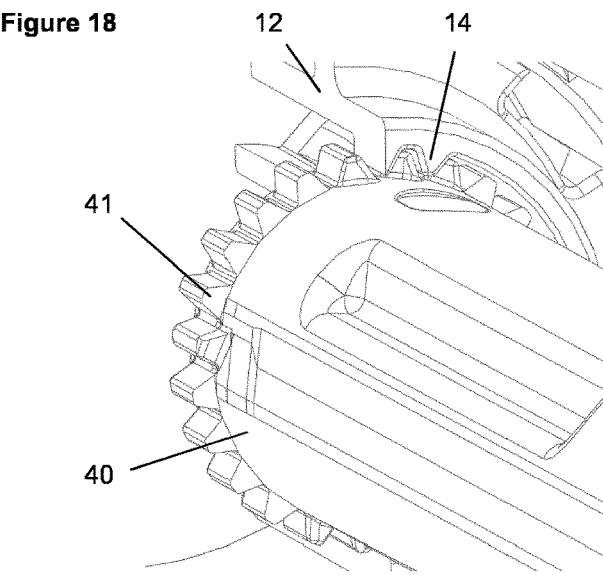
FIG. 18 shows an interface between the housing and the drive sleeve of the device of FIG. 1.

A splined tooth interface with the housing 10 prevents rotation of the drive sleeve 40 during dose setting. This interface which is shown in FIG. 18 in detail comprises a ring of radially extending outer teeth 41 at the distal end of drive sleeve 40 and corresponding radially extending inner teeth 14 of the housing component 10. When the button 70 is pressed, the drive sleeve 40 and housing 10 spline teeth 14, 41 are disengaged allowing the drive sleeve 40 to rotate relative to housing 10.

A further splined tooth interface with the number sleeve 60 is not engaged during dialing, but engages when the button 70 is pressed, preventing relative rotation between the drive sleeve 40 and number sleeve 60 during dispense. In the preferred embodiment shown in FIGS. 7a and 7b this interface comprises inwardly directed splines 61 on a flange 62 on the inner surface of the number sleeve 60 and a ring of radially extending outer splines 42 of drive sleeve 40. The corresponding splines 61, 42 are located on the number sleeve 60 and the drive sleeve 40, respectively, such that axial movement of the drive sleeve 40 relative to the (axially fixed) number sleeve 60 engages or disengages the splines to rotationally couple or decouple the drive sleeve 40 and the number sleeve 60.

Preferably, the splines 61, 42 are arranged such that they are decoupled when teeth 41 of drive sleeve 40 and inner teeth 14 of housing component 10 mesh and engage when teeth 41 and inner teeth 14 disengage. In a preferred embodiment the splines 61, 42 are longer in the axial direction compared with teeth 41, 14. This allows engagement of the splines 61, 42 shortly before disengagement of teeth 41, 14. In other words, the splines 61, 42 and the teeth 41, 14 are designed and arranged such that actuation of the button 70 rotationally constrains the drive sleeve 40 to the number sleeve 60 before the drive sleeve 40 is allowed to rotate relative to housing 10. Similarly, as the button 70 is released after dose dispensing axial movement of the drive sleeve 40 first rotationally constrains the drive sleeve 40 to the housing and thereafter decouples splines 61, 42. As an alternative to the corresponding splines 61, 42 teeth may be provided. As a further alternative or in addition to splines 61, 42, drive sleeve 40 and number sleeve 60 may be rotationally coupled to each other during dose dispensing via clutch plate 120.

Figure 19:
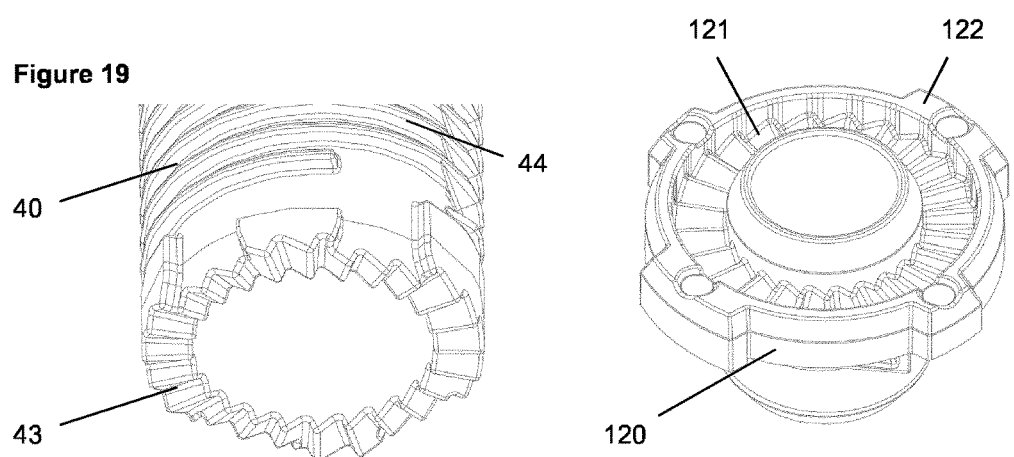
FIG. 19 shows an interface between the clutch plate and the drive sleeve of the device of FIG. 1.

An interface of the drive sleeve 40 which is shown in FIG. 19 comprises a ring of ratchet teeth 43 located at the proximal end face of drive sleeve 40 and a ring of corresponding ratchet teeth 121 of clutch plate 120.

Figure 20:
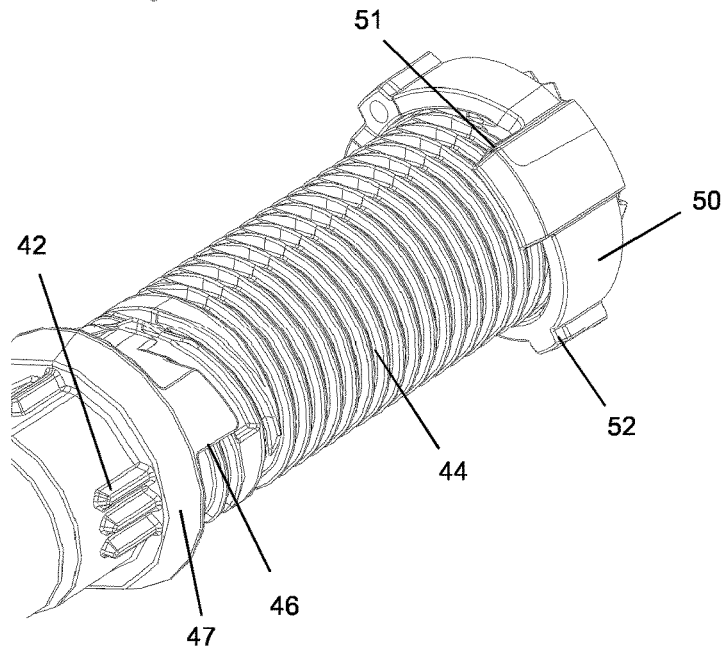
FIG. 20 shows a last dose mechanism of the device of FIG. 1.

The driver or drive sleeve 40 has a threaded section 44 providing a helical track for the nut 50 (FIG. 20). In addition, a last dose abutment or stop 46 is provided which may be the end of the thread 44 track or preferably a rotational hard stop for interaction with a corresponding last dose stop 51 of nut 50, thus limiting movement of the nut 50 on the thread 44. At least one longitudinal spline 45 engages a corresponding track of the lead screw 30. Further, the drive sleeve is provided with a ramp 47 interacting with a clicker arm 67 when the drive sleeve 40 is in its distal position during dose dispensing, i.e. when button 70 is depressed.

The last dose nut 50 is located between the number sleeve 60 and the drive sleeve 40. It is rotationally constrained to the number sleeve 60, via a splined interface (splines 52 on nut 50). It moves along a helical path relative to the drive sleeve 40, via a threaded interface (thread 44), when relative rotation occurs between the number sleeve 60 and drive sleeve 40 which is during dialing only. This is shown in FIG. 20. As an alternative, the nut 50 may be splined to the driver 40 and threaded to the number sleeve 60. In the embodiment shown in the Figures, the nut 50 is a full nut, but in alternative embodiments it may be a half nut, i.e. a component extending approximately 180° around the center axis of the device. A last dose stop 51 is provided engaging stop 46 of drive sleeve 40 when a dose is set corresponding to the remaining dispensable amount of medicament in the cartridge 100.

Figure 3:
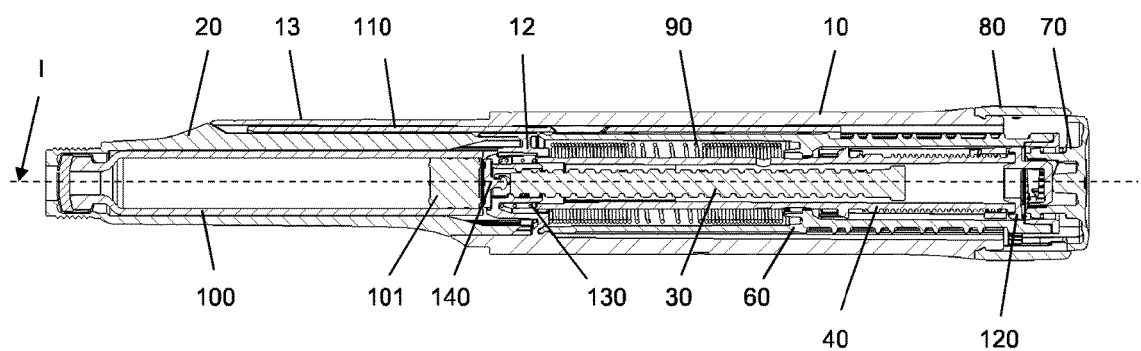
FIG. 3 shows a sectional view of the device of FIG. 1.

The dose indicator or number sleeve 60 is a tubular element as shown in FIGS. 2 and 3. The number sleeve 60 is rotated during dose setting (via dose selector 80) and dose correction and during dose dispensing by torsion spring 90. Together with gauge element 110 the number sleeve 60 defines a zero position ('at rest') and a maximum dose position. Thus, the number sleeve 60 may be seen as a dose setting member as may the dose selector.

For manufacturing reasons the number sleeve 60 of the embodiment shown in the Figures comprises a number sleeve lower 60a which is rigidly fixed to a number sleeve upper 60b during assembly to form the number sleeve 60. Number sleeve lower 60a and number sleeve upper 60b are separate components only to simplify number sleeve 60 mold tooling and assembly. As an alternative, the number sleeve 60 may be a unitary component. The number sleeve 60 is constrained to the housing 10 by features towards the distal end to allow rotation but not translation. The number sleeve lower 60a is marked with a sequence of numbers, which are visible through the gauge element 110 and the openings 11a, 11b in the housing 10, to denote the dialed dose of medicament.

Further, the number sleeve lower 60a has a portion with an outer thread 63 engaging the gauge element 110. End stops 64, 65 are provided at the opposite ends of thread 63 to limit relative movement with respect to the gauge element 110.

Figure 5:
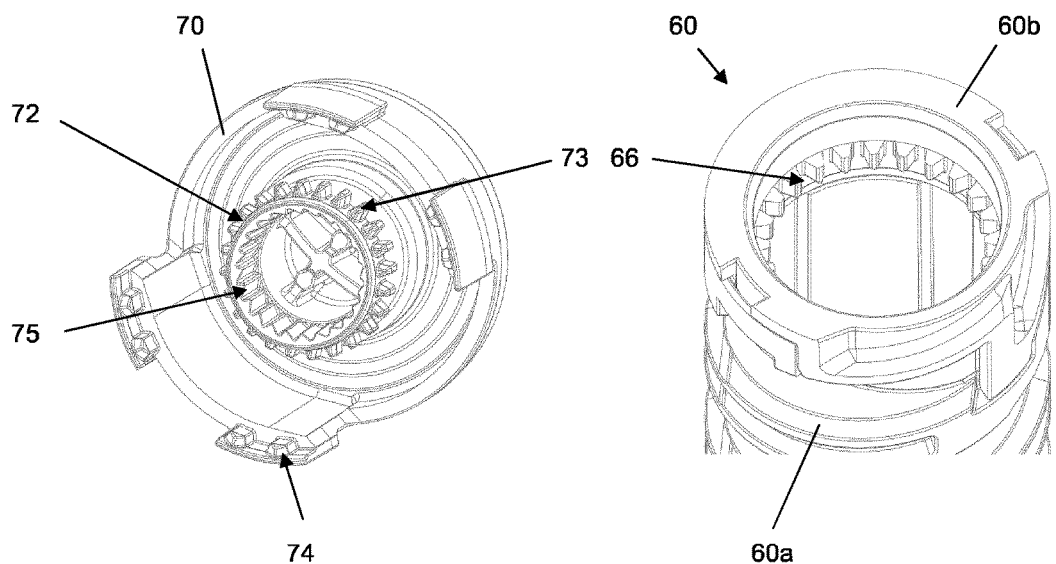
FIG. 5 shows an interface between the number sleeve and the button of the device of FIG. 1.

Clutch features which have the form of a ring of splines 66 in the embodiment of FIG. 5 are provided inwardly directed on number sleeve upper 60b for engagement with splines 73 of the button 70 during dose setting and dose correction. A clicker arm 67 is provided on the outer surface of number sleeve 60 which interacts with the drive sleeve 40 and the gauge member 110 for generating a feedback signal. In addition, the number sleeve lower 60a is rotationally constrained to the nut 50 and to the clutch plate 120 via a splined interface comprising at least one longitudinal spline.

An interface for attachment of the torsion spring 90 to the number sleeve lower 60a comprises large lead-ins and a groove feature 68 with a pocket 69 or anchor point for receiving a first coil or hook portion of the spring. The groove 68 has an end feature in the form of a ramp that is in interference with the hook portion 91 of the spring. The design of the groove 68 is such that the spring 90 may be received within the pocket 69 without interfering with the gauge element 110.

Figure 6:
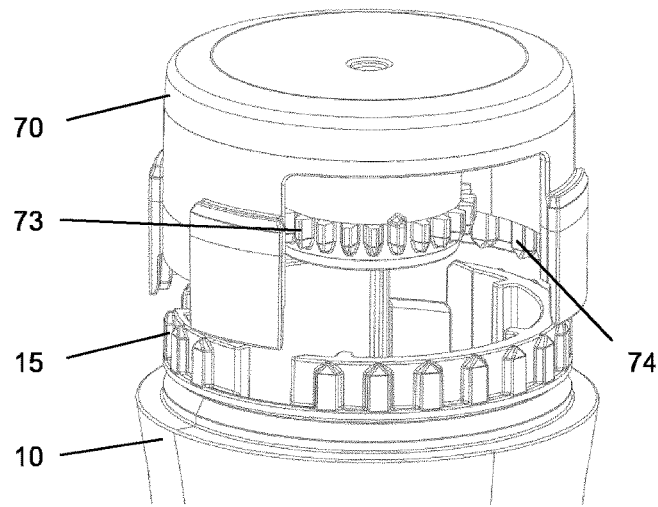
FIG. 6 shows an interface between the housing and the button of the device of FIG. 1.

The button 70 which forms the proximal end of the device is permanently splined to the dose selector 80. A central stem 71 extends distally from the proximal actuation face of the button 70. The stem 71 is provided with a flange 72 carrying the splines 73 for engagement with splines 66 of the number sleeve upper 60b (FIG. 5). Thus, it is also splined via splines 66, 73 (FIG. 5) to the number sleeve upper 60b when the button 70 is not pressed, but this spline interface is disconnected when the button 70 is pressed. The button 70 has a discontinuous annular skirt with splines 74. When the button 70 is pressed, splines 74 on the button 70 engage with splines on the housing 10 (FIG. 6), preventing rotation of the button 70 (and hence the dose selector 80) during dispense. These splines 74, 15 disengage when the button 70 is released, allowing a dose to be dialed. Further, a ring of ratchet teeth 75 is provided on the inner side of flange 72 (FIG. 9) for interaction with clutch plate 120.

The dose selector 80 is axially constrained to the housing 10. It is rotationally constrained, via the splined interface, to the button 70. This splined interface, which includes grooves interacting with spline features formed by the annular skirt of button 70, remains engaged irrespective of the dose button 70 axial positions. The dose selector 80 or dose dial grip is a sleeve-like component with a serrated outer skirt.

Figure 16:
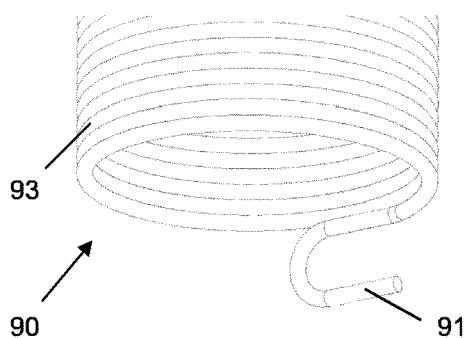
FIG. 16 shows a portion of the drive spring of the device of FIG. 1.

The torsion spring 90 is attached at its distal end to the housing 10 and at the other end to the number sleeve 60. The torsion spring 90 is located inside the number sleeve 60 and surrounds a distal portion of the drive sleeve 40. As shown in FIG. 16, the spring has a hook 91 at one end for attachment on the number sleeve 60. A similar hook end 92 is provided at the opposite end for attachment on the housing 10. The torsion spring 90 is pre-wound upon assembly, such that it applies a torque to the number sleeve 60 when the mechanism is at zero units dialed. The action of rotating the dose selector 80, to set a dose, rotates the number sleeve 60 relative to the housing 10, and charges the torsion spring 90 further.

The torsion spring 90 is formed from a helical wire with at least two different pitches. In FIG. 21, both ends are formed from 'closed' coils 93, i.e. the pitch equals the wire diameter and each coil contacts the adjacent coil. The central portion has 'open' coils 94, i.e. the coils do not contact each other.

The cartridge 100 is received in cartridge holder 20 (FIG. 3). The cartridge 100 may be a glass ampoule. A moveable rubber bung 101 may be received in the proximal end of the cartridge. The distal end of cartridge 100 is provided with a pierceable rubber seal which is held in place by a crimped annular metal band. The seal covers an outlet of the cartridge and prevents that fluid drug leaves the cartridge unless fluid communication is provided between the interior of the cartridge 100 and the outside. The drug is retained within the interior of the cartridge and can be dispensed from the cartridge by moving the bung 101 towards the outlet, provided fluid communication to the outside is established, e.g. by a needle assembly. In the embodiment depicted in the Figures, the cartridge 100 is a standard 1.5 ml cartridge. The device is designed to be disposable in that the cartridge 100 cannot be replaced by the user or health care professional. However, a reusable variant of the device could be provided by making the cartridge holder 20 removable and allowing backwinding of the lead screw 30 and the resetting of nut 50.

The gauge element 110 is constrained to prevent rotation but allow translation relative to the housing 10 via a splined interface. The gauge element 110 has a helical feature 111 on its inner surface which engages with the helical thread, which is preferably cut, in the number sleeve 60 such that rotation of the number sleeve 60 causes axial translation of the gauge element 110. This helical feature on the gauge element 110 also creates stop abutments 112, 113 against the end of the helical cut in the number sleeve 60 to limit the minimum and maximum dose that can be set.

The gauge element 110 has a generally plate or band like component having a central aperture 114 or window and two flanges 115, 116 extending on either side of the aperture. The flanges 115, 116 are preferably not transparent and thus shield or cover the number sleeve 60, whereas the aperture 114 or window allows viewing a portion of the number sleeve lower 60a. Further, gauge element 110 has a cam 117 and a recess 118 (FIGS. 11a-12c) interacting with the clicker arm 67 of the number sleeve 60 at the end of dose dispensing.

As can be seen in FIGS. 9 and 19, the clutch plate 120 is a ring-like component. The clutch plate 120 is splined to the number sleeve 60 via splines 122. It is also coupled to the drive sleeve 40 via a ratchet interface (ratchet teeth 43, 121). The ratchet provides a detented position between the number sleeve 60 and drive sleeve 40 corresponding to each dose unit, and engages different ramped tooth angles during clockwise and anti-clockwise relative rotation. A clicker arm 123 is provided on the clutch plate 120 for interaction with ratchet features 75 of the button.

The clutch spring 130 is a compression spring. The axial position of the drive sleeve 40, clutch plate 120 and button 70 is defined by the action of the clutch spring 130, which applies a force on the drive sleeve 40 in the proximal direction. This spring force is reacted via the drive sleeve 40, clutch plate 120, and button 70, and when 'at rest' it is further reacted through the dose selector 80 to the housing 10. The spring force ensures that the ratchet interface (ratchet teeth 43, 121) is always engaged. In the 'at rest' position, it also ensures that the button splines 73 are engaged with the number sleeve splines 66, and the drive sleeve teeth 41 are engaged with teeth 14 of the housing 10.

The bearing 140 is axially constrained to the piston rod 30 and acts on the bung 101 within the liquid medicament cartridge. It is axially clipped to the lead screw 30, but free to rotate. The bearing 140 comprises a disc 141 having a stem 142 extending in the proximal direction. The stem 142 has at its proximal end a convex contact surface 143. In addition, a recessed portion 144 is provided on the stem 142. The curvature of the convex contact surface 143 and the concave contact surface 33 is chosen such that the contact diameter between the bearing 140 and lead screw 30 is small to minimize the frictional losses at this interface. The design of the clip interface between bearing 140 and lead screw 30 permits the lead screw 30 to be assembled axially, from the proximal end and through the thread engagement to the housing 10, which simplifies assembly. In addition, this design allows a simple "open and shut" mold tooling for both components.

Figure 4A:
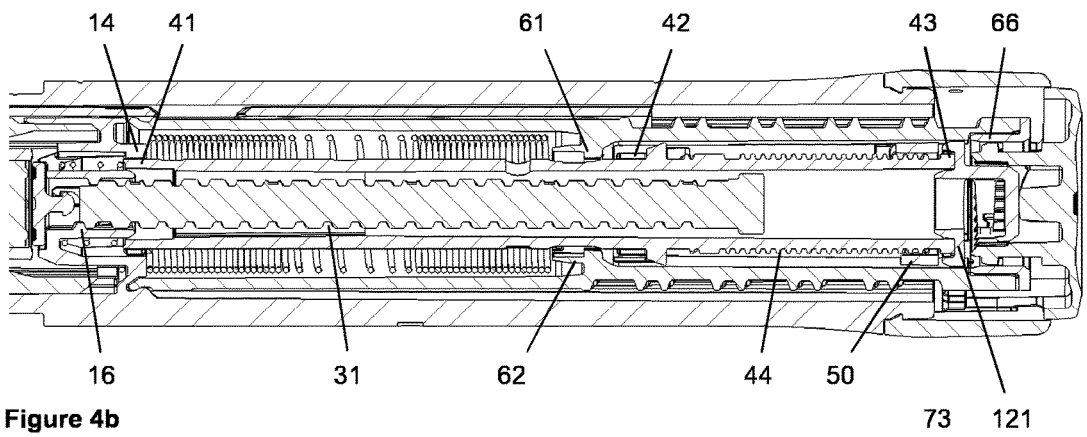
FIG. 4a shows an enlarged sectional view of a detail of the device of FIG. 1 in a dose setting mode.
Figure 4B:
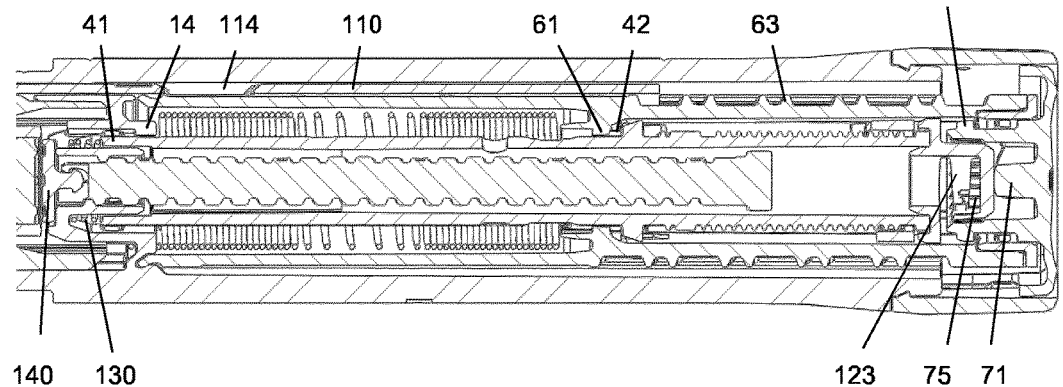
FIG. 4b shows an enlarged sectional view of a detail of the device of FIG. 1 in a dose dispensing mode.
Figure 17A:
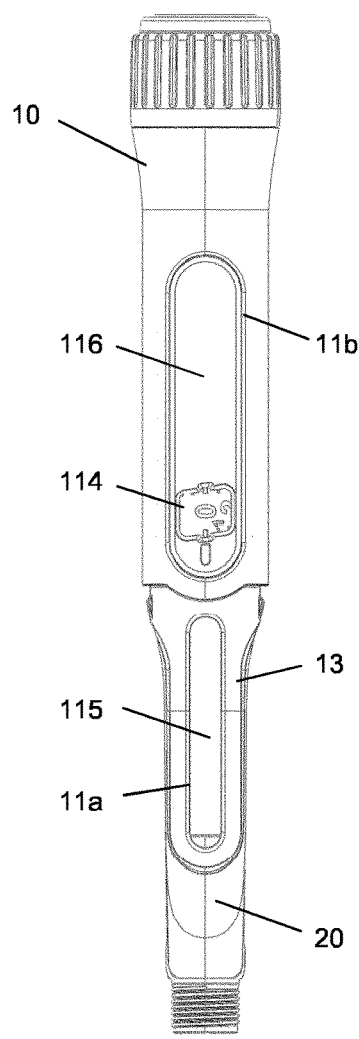
FIGS. 17a, b show top views of the device of FIG. 1 with 0 units dialed and with 96 units dialed.

With the device in the 'at rest' condition as shown in FIGS. 4a and 17a, the number sleeve 60 is positioned against its zero dose abutment 64, 113 with the gauge element 110 and the button 70 is not depressed. Dose marking '0' on the number sleeve 60 is visible through the windows 11b and 114 of the housing 10 and gauge element 110, respectively.

The torsion spring 90, which has a number of pre-wound turns applied to it during assembly of the device, applies a torque to the number sleeve 60 and is prevented from rotating by the zero dose abutment 64, 113. It is also possible to 'back-wind' the mechanism slightly due to an offset between the zero dose stop 64, 113 and the angular offset of the drive sleeve 40 spline teeth. This has the effect of preventing possible weepage when a dose is dialed and the zero dose abutment is disengaged.

The automated assembly of the torsion spring 90 into the number sleeve 60 can be achieved by incorporating large lead-ins and a groove feature to the number sleeve 60. As the torsion spring 90 is rotated during assembly, the hook end form 91 locates in the groove feature before engaging the anchor point in the number sleeve 60. To help to prevent the torsion spring 90 disengaging the anchor point 69 during subsequent assembly steps it is possible to create an interference between the torsion spring 90 and the number sleeve 60, or a one-way clip feature.

The user selects a variable dose of liquid medicament by rotating the dose selector 80 clockwise, which generates an identical rotation in the number sleeve 60. Rotation of the number sleeve 60 causes charging of the torsion spring 90, increasing the energy stored within it. As the number sleeve 60 rotates, the gauge element 110 translates axially due to its threaded engagement thereby showing the value of the dialed dose. The gauge element 110 has flanges 115, 116 either side of the window area 114 which cover the numbers printed on the number sleeve 60 adjacent to the dialed dose to ensure only the set dose number is made visible to the user.

A specific feature of this device is the inclusion of a visual feedback feature in addition to the discrete dose number display typical on devices of this type. The distal end (flange 115) of the gauge element 110 creates a sliding scale through a small window 11a in the housing 10. As an alternative, the sliding scale could be formed using a separate component engaged with the number sleeve 60 on a different helical track.

As a dose is set by the user, the gauge element 110 translates axially, the distance moved being proportional to the magnitude of the dose set. This feature gives clear feedback to the user regarding the approximate size of the dose set. The dispense speed of an auto-injector mechanism may be higher than for a manual injector device, so it may not be possible to read the numerical dose display during dispense. The gauge feature provides feedback to the user during dispense regarding dispense progress without the need to read the dose number itself. For example, the gauge display may be formed by an opaque element on the gauge element 110 revealing a contrasting colored component underneath. Alternatively, the revealable element may be printed with coarse dose numbers or other indices to provide more precise resolution. In addition, the gauge display simulates a syringe action during dose set and dispense.

Figure 17B:
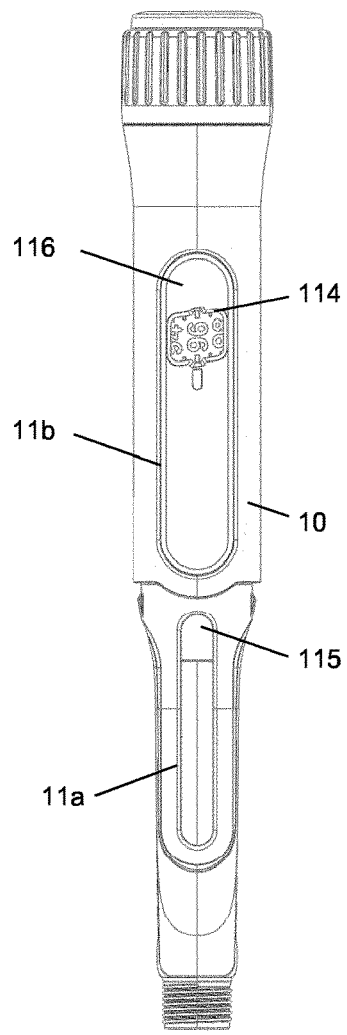

The openings 11a, 11b in the housing 10 allow the user to view the gauge feature and number display as shown in FIGS. 17a and 17b. To reduce dust ingress and prevent the user from touching moving parts, these openings 11a, 11b are covered by translucent windows. These windows may be separate components, but in this embodiment they are incorporated into the housing 10 using 'twin-shot' molding technology. A first shot of translucent material forms the internal features and the windows 11a, 11b, and then a 'second shot' of opaque material forms the outer cover of the housing 10.

The mechanism utilizes a dose selector 80 with an increased diameter relative to the housing 10 which aids dialing although this is not a requirement of the mechanism. This feature is particularly useful (but not essential) for an auto-injector mechanism where a power supply is charged during dose setting and the torque required to turn the dose selector 80 may be higher than for a non-auto injector device.

The drive sleeve 40 is prevented from rotating as the dose is set and the number sleeve 60 rotates due to the engagement of its splined teeth 41 with teeth 14 of the housing 10. Relative rotation must therefore occur between the clutch plate 120 and drive sleeve 40 via the ratchet interface 43, 121.

The user torque required to rotate the dose selector 80 is a sum of the torque required to wind up the torsion spring 90, and the torque required to overhaul the ratchet interface 43, 121. The clutch spring 130 is designed to provide an axial force to the ratchet interface 43, 121 and to bias the clutch plate 120 onto the drive sleeve 40. This axial load acts to maintain the ratchet teeth engagement of the clutch plate 120 and drive sleeve 40. The torque required to overhaul the ratchet 43, 121 in the dose set direction is a function of the axial load applied by the clutch spring 130, the clockwise ramp angle of the ratchet teeth 43, 121, the friction coefficient between the mating surfaces and the mean radius of the ratchet interface 43, 121.

As the user rotates the dose selector 80 sufficiently to increment the mechanism by one increment, the number sleeve 60 rotates relative to the drive sleeve 40 by one ratchet tooth. At this point the ratchet teeth 43, 121 re-engage into the next detented position. An audible click is generated by the ratchet re-engagement, and tactile feedback is given by the change in torque input required.

Relative rotation of the number sleeve 60 and the drive sleeve 40 is allowed as splines 42, 61 are disengaged during dose setting. This relative rotation also causes the last dose nut 50 to travel along its threaded path, towards its last dose abutment on the drive sleeve 40.

With no user torque applied to the dose selector 80, the number sleeve 60 is now prevented from rotating back under the torque applied by the torsion spring 90, solely by the ratchet interface 43, 121 between the clutch plate 120 and the drive sleeve 40. The torque necessary to overhaul the ratchet in the anti-clockwise direction is a function of the axial load applied by the clutch spring 130, the anti-clockwise ramp angle of the ratchet, the friction coefficient between the mating surfaces and the mean radius of the ratchet features. The torque necessary to overhaul the ratchet must be greater than the torque applied to the number sleeve 60 (and hence clutch plate 120) by the torsion spring 90. The ratchet ramp angle is therefore increased in the anti-clockwise direction to ensure this is the case whilst ensuring the dial-up torque is as low as possible.

The user may now choose to increase the selected dose by continuing to rotate the dose selector 80 in the clockwise direction. The process of overhauling the ratchet interface 43, 121 between the number sleeve 60 and drive sleeve 40 is repeated for each dose increment. Additional energy is stored within the torsion spring 90 for each dose increment and audible and tactile feedback is provided for each increment dialed by the re-engagement of the ratchet teeth. The torque required to rotate the dose selector 80 increases as the torque required to wind up the torsion spring 90 increases. The torque required to overhaul the ratchet in the anti-clockwise direction must therefore be greater than the torque applied to the number sleeve 60 by the torsion spring 90 when the maximum dose has been reached.

If the user continues to increase the selected dose until the maximum dose limit is reached, the number sleeve 60 engages with its maximum dose abutment 65 on the maximum dose abutment 112 of gauge element 110. This prevents further rotation of the number sleeve 60, clutch plate 120 and dose selector 80.

Depending on how many increments have already been delivered by the mechanism, during selection of a dose, the last dose nut 50 may contact its last dose abutment 51 with stop face 46 of the drive sleeve 40. The abutment prevents further relative rotation between the number sleeve 60 and the drive sleeve 40, and therefore limits the dose that can be selected. The position of the last dose nut 50 is determined by the total number of relative rotations between the number sleeve 60 and drive sleeve 40, which have occurred each time the user sets a dose.

With the mechanism in a state in which a dose has been selected, the user is able to deselect any number of increments from this dose. Deselecting a dose is achieved by the user rotating the dose selector 80 anti-clockwise. The torque applied to the dose selector 80 by the user is sufficient, when combined with the torque applied by the torsion spring 90, to overhaul the ratchet interface 43, 121 between the clutch plate 120 and drive sleeve 40 in the anti-clockwise direction. When the ratchet is overhauled, anti-clockwise rotation occurs in the number sleeve 60 (via the clutch plate 120), which returns the number sleeve 60 towards the zero dose position, and unwinds the torsion spring 90. The relative rotation between the number sleeve 60 and drive sleeve 40 causes the last dose nut 50 to return along its helical path, away from the last dose abutment.

With the mechanism in a state in which a dose has been selected, the user is able to activate the mechanism to commence delivery of a dose. Delivery of a dose is initiated by the user depressing the button 70 axially in the distal direction.

When the button 70 is depressed, splines between the button 70 and number sleeve 60 are disengaged, rotationally disconnecting the button 70 and dose selector 80 from the delivery mechanism, i.e. from number sleeve 60, gauge element 110 and torsion spring 90. Splines 74 on the button 70 engage with splines 15 on the housing 10, preventing rotation of the button 70 (and hence the dose selector 80) during dispense. As the button 70 is stationary during dispense, it can be used in the dispense clicker mechanism as shown in FIG. 9. A stop feature in the housing 10 limits axial travel of the button 70 and reacts any axial abuse loads applied by the user, reducing the risk of damaging internal components.

Figure 7A:
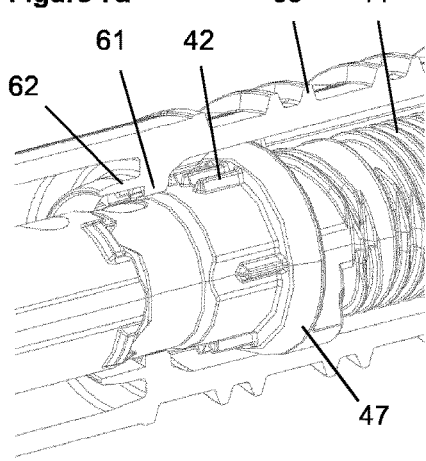
FIGS. 7a, b show an interface between the number sleeve and the drive sleeve of the device of FIG. 1 in the dose setting mode and in the dose dispensing mode.
Figure 7B:
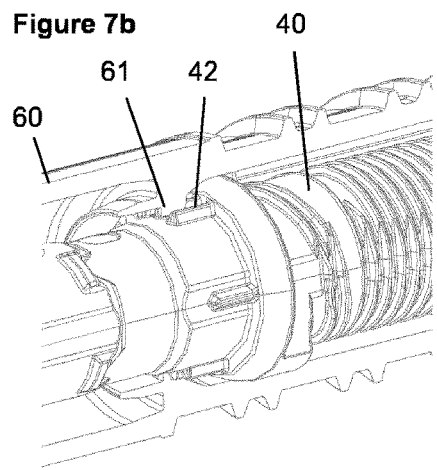

The clutch plate 120 and drive sleeve 40 travel axially with the button 70. This engages the splined tooth interface 42, 61 between the drive sleeve 40 and number sleeve 60 as shown in FIGS. 7a (splines 42, 61 disengaged) and 7b (splines 42, 61 engaged), preventing relative rotation between the drive sleeve 40 and number sleeve 60 during dispense. The splined tooth interface 41, 14 between the drive sleeve 40 and the housing 10 disengages, so the drive sleeve 40 can now rotate and is driven by the torsion spring 90 via the number sleeve 60, and clutch plate 120.

Rotation of the drive sleeve 40 causes the piston rod 30 to rotate due to their splined engagement, and the piston rod 30 then advances due to its threaded engagement to the housing 10. The number sleeve 60 rotation also causes the gauge element 110 to traverse axially back to its zero position whereby the zero dose abutment 64, 113 stops the mechanism.

The bearing 140 is axially clipped to the piston rod 30, but free to rotate. Since the bearing 140 is in direct contact with the bung 101, it does not rotate as the piston rod 30 rotates and advances during dose dispense. As described above, the contact diameter between the bearing 140 and piston rod 30 is small to minimize the frictional losses at this interface. The design of the piston rod 30 and bearing 140 eliminates delicate clip features or large contact diameters present on previous concepts. This embodiment also allows the piston rod 30 to be assembled axially, from the proximal end and through the thread engagement to the housing 10, which simplifies assembly.

Tactile feedback during dose dispense is provided via the compliant cantilever clicker arm 123 integrated into the clutch plate 120. This arm 123 interfaces radially with ratchet features 75 on the inner surface of the button 70, whereby the ratchet tooth spacing corresponds to the number sleeve 60 rotation required for a single increment dispense. During dispense, as the number sleeve 60 rotates and the button 70 is rotationally coupled to the housing 10, the ratchet features 75 engage with the clicker arm 123 to produce an audible click with each dose increment delivered.

Delivery of a dose continues via the mechanical interactions described above while the user continues to depress the button 70. If the user releases the button 70, the clutch spring 130 returns the drive sleeve 40 to its 'at rest' position (together with the clutch plate 120 and button 70), engaging the splines 14, 41 between the drive sleeve 40 and housing 10, preventing further rotation and stopping dose delivery.

During delivery of a dose, the drive sleeve 40 and number sleeve 60 rotate together, so that no relative motion in the last dose nut 50 occurs. The last dose nut 50 therefore travels axially relative to the drive sleeve 40 during dialing only.

Once the delivery of a dose is stopped, by the number sleeve 60 returning to the zero dose abutment, the user may release the button 70, which will re-engage the spline teeth 14, 41 between the drive sleeve 40 and housing 10. The mechanism is now returned to the 'at rest' condition.

It is possible to angle the spline teeth 14, 41 on either the drive sleeve 40 or housing 10 so that when the button 70 is released the re-engagement of the spline teeth 14, 41 fractionally 'backwinds' the drive sleeve 40 thereby removing the engagement of the number sleeve 60 to the zero dose stop abutment on the gauge element 110. This compensates for the effect of clearances in the mechanism (for example due to tolerances) which could otherwise lead to slight advancement of the piston rod 30 and medicament dispense when the device is dialed for the subsequent dose due to the number sleeve 60 zero dose stop not restraining the mechanism and instead the restraint returning to the splines between the drive sleeve 40 and housing 10.

At the end of dose dispensing, additional audible feedback is provided in the form of a 'click', distinct from the 'clicks' provided during dispense, to inform the user that the device has returned to its zero position via the interaction of the clicker arm 67 on the number sleeve 60 with the ramp 47 on the drive sleeve 40 and the cam 117 and the recess 118 on the gauge element 110. This embodiment allows feedback to only be created at the end of dose delivery and not created if the device is dialed back to, or away from, the zero position.

FIG. 11a shows the position of the click features when the device is in the 'at rest' condition, with zero units dialed and the button 70 not depressed. It can be seen that the cam feature 117 on the gauge element 110 does not contact the clicker arm 67 on the number sleeve 60 when the button 70 is in the 'at rest' condition, so during storage or dialing the clicker arm 67 is not deflected.

During dialing, the gauge element 110 translates in the proximal direction, so the cam 117 is no longer aligned axially with the clicker arm 67. At the start of dose delivery when the drive sleeve 40 translates in the distal direction, the ramp 47 on the drive sleeve 40 pushes the clicker arm 67 radially outwards. During dose delivery, the gauge element 110 translates back in the distal direction, and towards the end of dose delivery, the clicker arm 67 contacts the cam 117 on the gauge element 110. For small doses, the cam 117 and clicker arm 67 will be in contact at the start of the dose. FIGS. 11b to 12c show the component interactions. After dose delivery, the button 70 is released and the end of dose mechanism returns to its 'at rest' position.

In FIG. 11b a dose is dialed and approximately one full dial turn is applied to number sleeve 60. Gauge element 110 is axially translated away from zero-unit position, so that cam 117 is no longer aligned axially with clicker arm 67. FIG. 11c shows the start of dispensing, when button 70 is depressed to initiate dose dispense and which causes the drive sleeve 70 to translate axially. The ramp 47 on the drive sleeve 40 pushes the clicker arm 67 radially out and into radial alignment with the cam 117 on the gauge element 110.

Figure 12A:
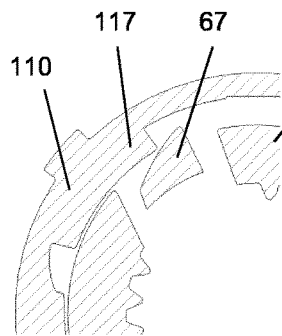
FIGS. 12a-c show in enlarged sectional views the sequence of generating a click at the end of dose dispensing of the device of FIG. 1.
Figure 12B:
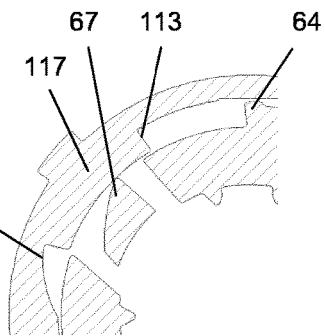
Figure 12C:
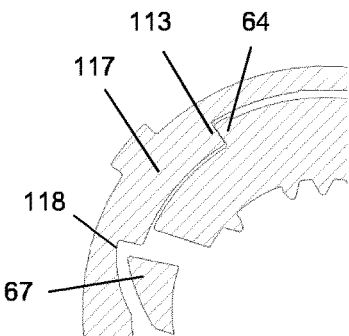
Figure 13:
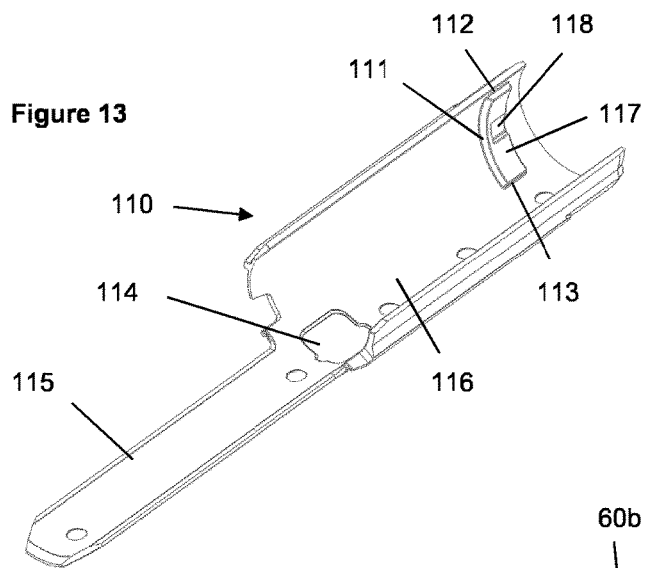
FIG. 13 shows the gauge element of the device of FIG. 1.
Figure 14:
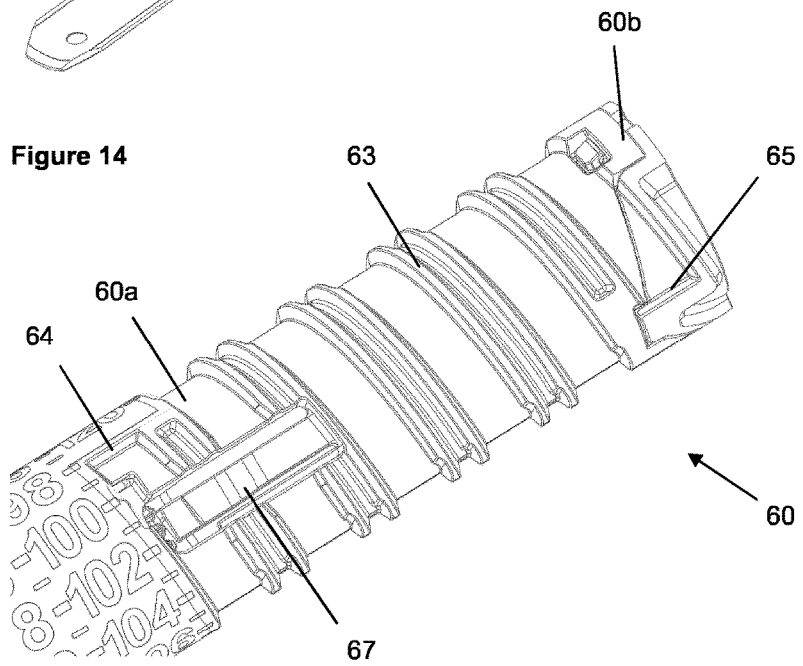
FIG. 14 shows a portion of the number sleeve of the device of FIG. 1.
Figure 15:
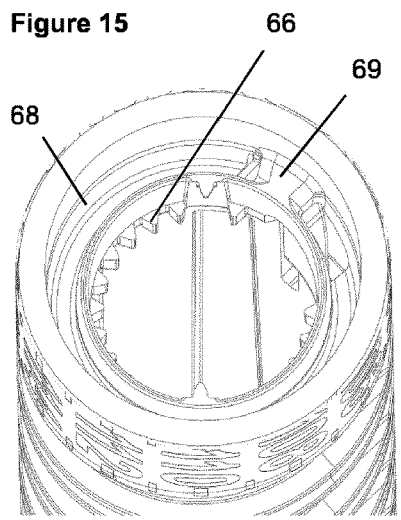
FIG. 15 shows a further portion of the number sleeve of the device of FIG. 1.

FIG. 12a shows the mechanism at the end of dose dispensing with approximately 4 units remaining. The gauge element 110 returns axially towards its zero-unit position, so that cam 117 aligns axially with clicker arm 67. Rotation of number sleeve 60 causes clicker arm 67 to contact cam 117 such that clicker arm 67 is pushed radially inwards. With approximately 2 units remaining the number sleeve 60 rotates further and clicker arm 67 follows the profile of cam 117 (FIG. 12b). This radial deflection 'charges' clicker arm 67 storing elastic energy. In FIG. 12c dispensing is completed as the number sleeve 60 reaches its zero-unit rotational position. The clicker arm 67 drops off the sharp edge of cam 117 into recess 118. Elastic energy is released causing clicker arm 67 to spring radially outwards to contact cam 117 and create a distinct 'click'.

In an embodiment, the lead screw 30 advances by a fixed displacement for each revolution of the drive sleeve 40. In other embodiments, the rate of displacement may vary. For example, the lead screw 30 may advance a large displacement per revolution to dispense a first amount of medicament from the cartridge 100 and then a smaller displacement per revolution to dispense the rest of the cartridge 100. This is advantageous, as it can compensate for the fact that the first dose dispensed from the cartridge 100 often has a lower volume than other doses, for a given displacement of the mechanism.

FIG. 22 shows three embodiments with the threads 16 of the housing 10 and the threads 31 of the lead screw 30 projected around the circumference. Arrow R indicates the direction of revolution of the lead screw 30 with respect to housing 10 for all three views.

View (a) shows the principal embodiment, where the pitch is equal on the housing 10 and lead screw 30, so the lead screw 30 advances a fixed amount for every revolution of the drive sleeve 40. In view (b), the first turn of thread 31 on the lead screw 30 has a large pitch, and the other turns have a small pitch. During the first revolution, the lead screw 30 displacement depends on the large pitch of the first turn of thread 31 on the lead screw 30, so it displaces a large amount per revolution. For subsequent revolutions the lead screw 30 displacement depends on the smaller pitch of the lead screw thread 31, so it displaces a smaller amount. In view (c), the housing 10 thread 16 has a larger pitch than the lead screw 30. During the first revolution, the lead screw 30 displacement depends on the pitch of the housing thread 16, so it displaces a large amount per revolution. For subsequent revolutions the lead screw 30 displacement depends on the pitch of the lead screw thread 31, so it displaces a smaller amount.

It has been found that, when dispensing the first liquid drug or medicament from the cartridge of a drug delivery device, the required force can be substantially higher than the one for subsequent dispenses. This is probably due to bung stiction/adhesion effects of the bung within the cartridge. The stiction/adhesive effects are particularly pronounced when the cartridge has been stored for a while. Consequently, the force which is required to move the bung in the cartridge for the first time when the cartridge is higher in an as-assembled condition, e.g. as provided by the manufacturer and all of the drug or medicament which was once filled into the cartridge is still present in the cartridge, than when drug has already dispensed from the device.

In the following, different solutions are described which provide a higher dispensing force, particularly a higher maximal dispensing force, when the bung is in the initial position as provided by the manufacturer than during subsequent dispensing operations, for example during the dispensing of the second or third dose. The dispensing force, after the high initial dispensing force, may be constantly lower for any subsequent dose after the dispensing force, particularly the maximal dispensing force, has been lowered once from the initial high value to the subsequent or regular value.

Solutions of this kind are particularly advantageous if a mechanical energy storage member such as spring 90 is used in the device to provide the driving force which is required to move the bung to dispense the drug from the cartridge. If the drive mechanism can be designed such that the initial driving or dispensing force is higher than during subsequent dispensing actions without changing the spring design and spring assembly, the requirements which the energy storage member has to meet may not be as stringent. For example, a spring of lesser spring strength may be used. This has a couple of advantages as, for example, the energy which has to be applied by the user to load the energy storage member during a dose setting operation is less as the regular driving force required to get the bung to move subsequent to the initial driving of the bung away from its initial position is lower and, thus, operation of the device is more effortless for the user as compared to a higher strength spring. Additionally, weaker springs may be more cost effective and also smaller. In the case of a torsion spring 90, as is used in the device as described above, the dialing torque which has to be applied by the user to set up a dose, can be reduced if the initial driving force can be increased by means of design of the drive mechanism over the regular driving force which is required subsequent to dispensing of the first liquid. Reduction in size of the spring and a lower spring strength of the spring which is used as energy storage member may also result in an increased device robustness as forces and torques exerted in the drug delivery device are generally reduced subsequent to the initial dispensing.

The proposed solutions may be applied in any drug delivery device, such as a pen injector, particularly a drug delivery device for delivery of a variable, user-selectable dose of medicament or drug into the body, such as by means of a needle. One exemplary embodiment to which the solutions described herein may be applied is the drug delivery device described in conjunction with FIGS. 1 to 22c. Consequently, some of the concepts disclosed herein are described in relation to the drug delivery device mentioned above, but it should be kept in mind that the solutions are not only applicable to these drug delivery devices but also to other drug delivery devices which employ a drive mechanism which transfers a force within a drug delivery device to a bung to move the bung with respect to the cartridge, and, particularly, to automatic dispensing devices where no user exerted force contributes to the dispensing force during the dispensing of the dose.

Figure 23A:
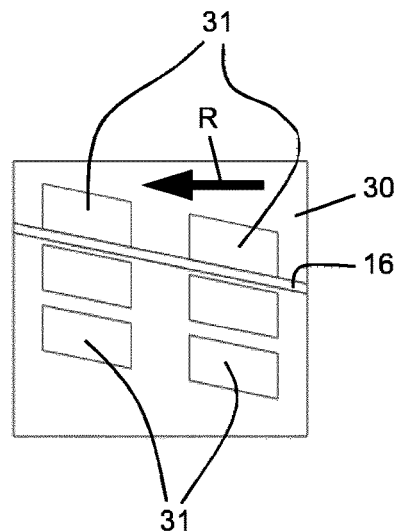
FIG. 23a, b show again different embodiments of the threads between the piston rod and the housing of the device of FIG. 1, where the embodiment in FIG. 23b provides for an initially increased driving force.
Figure 23B:
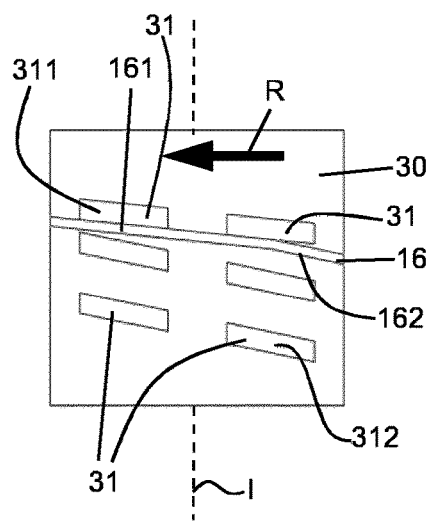

FIGS. 23a and 23b disclose one embodiment which is suitable to provide a higher initial driving force for dispensing the first amount of drug from the cartridge than for dispensing the subsequent drug, i.e. when the initial bung stiction/adhesion of the bung 101 at the inner wall of the cartridge 100 has been overcome.

FIGS. 23a and 23b show schematic views of the piston rod or lead screw 30 with its thread 31 and the inner thread 16 of the housing 10 similar to FIGS. 22a-c. FIG. 23a, which essentially corresponds to FIG. 22a, shows a design where a driving force, provided a given torque is transferred from the torsion spring 90 to the piston rod 30, is constant throughout the travel from the piston rod from its initial position in the distal direction to deliver drug from the cartridge to its end position, when the piston rod can no longer be moved into the distal direction, e.g. due to the last dose stop mechanism as described above. Thread 31 has a constant pitch and/or lead in FIG. 23a. When the piston rod is rotated to the left—as indicated by arrow R—it translates in the distal direction on account of the cooperation of thread 31 with thread 16 in the housing 10. The distal direction is the upper direction in FIG. 23a.

In FIG. 23b the piston rod 30 is also advanced in the distal direction, i.e. upwards, when rotating to the left with respect to the inner thread 16. In order to advance the piston rod 30 in the distal direction, a proximal surface of the thread 31 may contact a distal surface of the thread 16. However, in contrast to FIG. 23a, the thread 31 on the piston rod 30 has a variable pitch and/or lead. Therefore, the distance by which the piston rod is displaced distally with respect to the housing in one revolution varies, depending on the particular pitch or lead of that section of the thread 31 which currently interacts with thread. Particularly, the distance between two consecutive windings of the thread may vary in the axial direction. The thread 31 is designed such that the pitch and/or lead of the thread is smaller in a distal (end) section 311 of the thread 31 than in a proximal section 312 of the thread 31 which may follow after the distal section 311. The distal section 311 and the proximal section 312 are connected via an intermediate section where the lead and/or pitch changes from a first value in the distal section to a second value in the proximal section 312. The first value is expediently smaller than the second value. In the proximal section 312 and/or in the distal section 311 the pitch and/or lead are preferably constant.

The finer pitch and/or lower lead of the thread 31 in the distal end section 311 result in a first portion of rotation of the piston rod 30 with respect to the inner thread 16 having a lower rate of piston rod advancement than the following rotations. The finer pitch and/or lower lead results in a lower rate of advancement and means that for a given torque applied by the spring 90, which causes the piston rod to rotate, the resulting axial force generated by the piston rod will be greater than for a thread with coarser pitch or greater lead.

Preferably, there is only one change in pitch and/or lead of the thread 31, thus ensuring a conform or constant axial advancement of the piston rod 30 when the thread 16 cooperates with the proximal section 312. The driving force is increased only initially to overcome initial bung stiction.

The inner thread 16 which, in cooperation with the thread 31, establishes the threaded interface of the piston rod 31 and the housing 10, is adjusted to the varying pitch and/or lead in the thread 31 of the piston rod in the FIG. 23b embodiment.

The thread 16 of the housing is adapted to cooperate with a thread having a varying pitch and/or lead. For this purpose, an angle of inclination of a surface of the thread 16 which is adapted to cooperate with the piston rod 30, preferably a distal facing surface of the thread 16, i.e. the upper surface in FIG. 23b, with respect to the longitudinal axis 1 of the piston rod 30 changes. Particularly, the smaller angle of the two angles which the thread 16, particularly the distal facing surface thereof, defines with the longitudinal axis 1 when seen in projection onto the longitudinal axis may increase in the direction of rotation of the piston rod relative to the inner thread 16 as indicated by the arrow R in FIG. 23b. Furthermore, the clearance between two consecutive windings of the thread 31 is greater, on account of the specific angled design of the surface of the thread in FIG. 23b than in FIG. 23a, as, in FIG. 23b, the modified design of the thread 16 has to be taken into account. In FIG. 23a, both threads, i.e. thread 16 and thread 31, have equal pitches and/or leads. In FIG. 23b, the inner thread 16 may have one section 161, which is adapted to cooperate with the distal section 311 of the thread 31, and another section 162 which is adapted to cooperate with the proximal section 312 of the thread 31. The section 162 may precede the section 161 as seen along the rotation direction. Sections 161 and 162, particularly the distal surfaces of the respective sections, may be arranged angled—defining an angle different from 180°—with respect to each other. The distal surface of the respective section 161 or 162 may be smooth. Preferably, the angle with respect to the axis 1 which is defined by the section 161, preferably the distal surface thereof, corresponds to the angle defined by the distal section 311 of the thread 31 and the axis 1 when seen in projection on the axis 1. Section 162, preferably the distal surface thereof, forms an angle with the axis 1 which corresponds to the angle which the proximal section 312 forms with the axis 1 as seen in projection on the axis 1.

Figure 24:
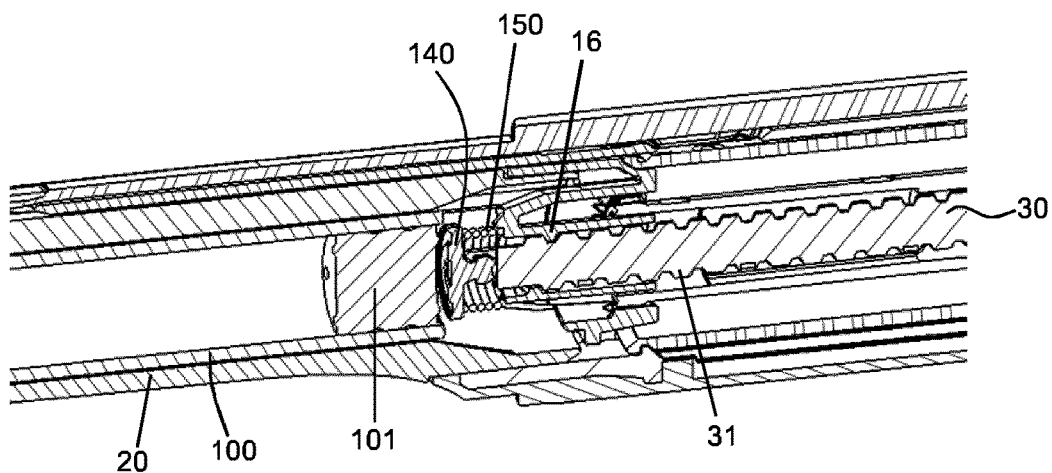
FIG. 24 shows an embodiment of the device of FIG. 1, which uses a supplemental storage member to provide an initially increased driving force.

Another solution to the problem of providing an initial high driving force to overcome the initial bung stiction is described in conjunction with FIG. 24. This solution can be applied instead of or together with the solution described in conjunction with FIG. 23b. In FIG. 24, a supplemental storage member or auxiliary storage member 150 is used. The supplemental storage member 150 may be a spring, such as a compression spring, as depicted in FIG. 24, a leaf spring or a washer spring.

The supplemental storage member 150 has energy stored therein in the initial position of the piston rod 30 where the device has not yet been operated, i.e. the piston rod 30 has not been moved yet. This situation is depicted in FIG. 24. The stored energy may be used, in addition to the energy provided by the spring 90, to move the bung 101 away from the initial position depicted in FIG. 24 and, consequently, may assist the force exerted by the spring 90 to overcome the initial bung stiction.

The energy stored in supplemental storage member 150 is preferably less than the one required to move the bung 101 away from its initial position. In its initial position, the bearing may abut the bung. Consequently, excessive pressurization of the drug within the cartridge can be avoided, if the piston rod 30 contacts the bung 101 in the initial position of piston rod and bung and the energy stored in the member is not sufficient to provide a force to move the bung. Thus, in this case, when a needle is attached to the device, no fluid may drip unintentionally out of the device as the supplemental storage member does not have enough energy within it.

Alternatively, in the initial position of the piston rod 30, there may be a clearance between the distal surface of the piston rod 30 or bearing 140 and the proximal face of the bung 101. In other words, instead of being mechanically coupled to the bung in the initial position, the piston rod may be mechanically decoupled from the bung in the initial position. Thus, before the bung 101 can be driven by the piston rod 30, mechanical coupling has to be established, e.g. by moving the piston rod towards the bung to close the clearance.

The supplemental storage member 150 biases the piston rod 30 into the distal direction. For this purpose, the supplemental storage member 150 may be arranged in a biased state between a surface of the housing 10, particular a distal surface, and a surface of the bearing 140, particular a proximal surface. As the bearing 140 is connected to the piston rod 30 as is depicted in FIG. 8, the supplemental storage member biases the piston rod 31 in the distal direction such that the force exerted by the supplemental storage member 150 onto the bearing 140 also acts on the piston rod. The force exerted by the supplemental storage member 150 may contribute to the initial driving force together with the energy storage member, i.e. spring 90. However, the supplemental storage member preferably has less energy stored in it than which would be required to move the piston rod to close the clearance between bearing 140 and bung 101. Thus, a reliable clearance may be established between piston rod and bung in the initial position. Also, it can be avoided that the drug in the cartridge is significantly pressurized. The maximal driving force providable by the spring 90 is preferably less than the one which is required to move the bung away from the initial position. Thus, the energy stored in the supplemental storage member is required to move the bung away from its initial position in order to dispense drug from the cartridge. Consequently the spring 90 can be chosen to be appropriately weak with the associated advantages and assisted by a second spring 150 which is also not too strong, big or expensive as supplemental storage member 150 to overcome the initial bung stiction.

As the supplemental storage member acts on the bearing 140, it biases the bearing away from the piston rod 31 such that a distal surface 145, e.g. a surface of a radial protrusion of the bearing which is received between the clip arms 32 of the piston rod 30, contacts a proximal surface 34 of the piston rod 30, such as the proximal surface of a radially inwardly protruding portion of the clip arms 32. As compared to the situation depicted in FIG. 8, the bearing is moved to the left until surfaces 145 and 34 abut in the situation depicted in FIG. 24. Consequently, in the situation depicted in FIG. 24, the piston rod 30 and the bearing 140 are under tension with respect to each other. The state of tension is in contrast to the situation when the bung 101 has been contacted by the bearing 140 and drug is being dispensed. During this state, the bearing and the piston rod are in a state of compression, i.e. the surfaces 33 and 143 abut as depicted in FIG. 8. It is advantageous that, in order to guarantee a constant dispensing state of the device from the first dose onwards, that drug is only dispensed from the device when the bearing and the piston rod are in the state of compression where a proximally facing surface of the bearing 140 abuts a distally facing surface of the piston rod 30. This can be achieved by choosing the supplemental energy member such that the force, expediently the maximal force, transferrable by the supplemental energy member to the bung is less than the one required to move the bung away from the initial position such that bearing and piston rod are moved into the compressed state first and, afterwards, the bung is moved on account of the additional force provided by the spring 90. This can increase the dose accuracy, as otherwise the transition from the tension state to the compression state of bearing and piston rod would not occur until the bearing separates from the compression spring, which could reduce the accuracy of the dose which is dispensed. Consequently, it is beneficial that the piston rod 30 and the bearing 140 are in the compression state as the first drug is dispensed from the cartridge even with the supplemental storage member 150 acting on the bearing 140. This, as noted above, can be achieved by choosing a spring for the storage member 150 which is weaker than the bung stiction. Consequently, the supplemental storage member is chosen to only supplement the axial force transferred by means of the piston rod to the bung without being strong enough on its own to overcome the bung stiction and dispense the drug independently. The conversion from the state of tension to the state of compression should occur before the end of the first dispense movement of the bung and, ideally, before the start of the first dispense movement.

The axial thrust achievable by the supplemental storage member, e.g. the length of the relaxed compression spring, is chosen to be sufficient to allow the supplemental storage member to act upon the bearing over the distance, preferably only over the distance, during which initial bung stiction effects are present which increase the force required to move the bung substantially. Beyond this point, the bearing and the supplemental storage member separate and the supplemental storage member plays no further role in the operation of the device.

Alternatively to a spring as the supplemental storage member or as an additional supplemental storage member, a cartridge filled with pressurized gas could be positioned between the piston rod 30 or the bearing 140 and the bung 101 in order to provide the supplemental force to assist the energy storage member 90, for example when the pressurized gas expands once an outer shell of the cartridge has been destroyed or punctuated to provide fluid communication between the interior of the cartridge and the outside, which may be effected by the force the piston rod transfers to the outer shell of the cartridge. This is not explicitly shown in figures.

A further approach which can be used to provide an initially increased dispensing force is the provision of a second thread on the piston rod 30 in addition to the thread 31 which couples the piston rod to the housing 10. This is not explicitly shown in the figures. Via the second thread, the piston rod in its initial position may be coupled to the bearing 140, for example. The second thread has a smaller pitch and/or lead than the thread 31. The second thread may be provided in a distal section of the piston rod and may, in the initial position of the piston rod, be threadedly coupled to the bearing. The second thread may be, in the proximal direction, followed by a section of the piston rod which cannot threadedly interact with the bearing, e.g. an unthreaded section. Proximally with respect to this section, the section of the piston rod with the thread 31 may be provided. The bearing may comprise a proximal threaded section designed to threadedly interact with the second thread and a distal unthreaded section which is arranged subsequent to the threaded section in the distal direction.

In the initial position of the piston rod 30 the bearing 140 may be in contact with the bung or arranged at a distance therefrom. Consequently, during the first part of the movement of the piston rod the clearance between bearing and bung may be closed, depending on whether there is a clearance. Once the bearing is in contact with the bung and the piston rod rotates relative to the housing, the piston rod also rotates relative to the bearing and is in threaded interaction with the bearing. Due to the two threaded interfaces between the housing and the piston rod and between the bearing and the piston with different pitches and/or leads, the force acting on the bung is increased as long as both threaded interfaces are active. Once the section of the piston rod with the second thread has moved past the threaded section in the bearing in the distal direction, there is no longer a threaded interaction of bearing and piston rod, for example because the distal threaded section of the piston rod with the second thread is arranged within the unthreaded section of the bearing and the unthreaded section of the piston rod is arranged within the threaded section of the bearing. Consequently, the second threaded interface is inactivated and the dispensing force is no longer increased over the force transferred by the piston rod via the first threaded interface. It is advantageous to design the second thread with respect to pitch, lead and/or length such that an increased dispensing force is only provided when the increased initial bung stiction has to be overcome as outlined above for the other disclosed approaches in order to provide an increased initial dispensing force.

All of the approaches described above permit the use of a weaker spring 90 in the device of FIG. 1 while still delivering sufficient force at the start of a cartridge to overcome bung stiction. A weak spring is feasible as beyond the start of the cartridge, once initial stiction has been overcome, the dispense force requirement are less. The ability to choose a weaker torsion spring has many potential benefits including: lower dialing torque for the user, smaller, cheaper torsion spring and, consequently, a smaller and cheaper device and increased device robustness as forces and torques exerted within the device are generally reduced.

It should be noted that the approaches described above are not only suitable for a rotating piston rod or lead screw which rotates relative to the body, but could also be applied to a piston rod or lead screw which is axially advanced by means of a rotating nut, where the piston rod or lead screw is secured against rotation with respect to the housing. Consequently, the approaches above may also be suitable for non-rotating piston rods. It may not even be necessarily a threaded piston rod or lead screw which is used. Especially the approach described in conjunction with FIG. 24 with the supplemental storage member could also be used for a non-rotating non-threaded piston rod, which is embodied as a toothed rod, for example.

REFERENCE NUMERALS

10 housing
11a, b opening 12 flange-like inner wall
13 strip
14 teeth
15 spline
16 inner thread
161 section of the inner thread
162 another section of the inner thread
20 cartridge holder
30 lead screw (piston rod)
31 outer thread
311 distal section
312 proximal section
32 clip arm
33 concave contact surface
34 surface
40 driver (axially movable drive sleeve)
41 teeth
42 spline
43 ratchet teeth
44 threaded section
45 spline
46 last dose stop
47 ramp
50 nut
51 last dose stop
52 spline
60 dose indicator (number sleeve)
60a number sleeve lower
60b number sleeve upper
61 spline
62 flange
63 outer thread
64, 65 end stop
66 spline
67 clicker arm
68 groove
69 anchor point
70 button
71 stem
72 flange
73, 74 spline
75 ratchet teeth
80 dose selector
90 torsion spring
91, 92 hook
93, 94 coil
100 cartridge
101 bung
110 gauge element
111 helical feature
112, 113 stop
114 aperture
115, 116 flange
117 cam
118 recess
120 clutch plate
121 ratchet teeth
122 protrusion
123 clicker arm
130 clutch spring
140 bearing
141 disc
142 stem
143 convex contact surface
144 recessed portion
145 surface
150 supplemental storage member
I longitudinal axis
R direction of revolution

The invention claimed is:

1. A drug delivery device, comprising:
a housing,
a cartridge containing a drug in a quantity sufficient for a plurality of doses of the drug,
a bung movably retained within the cartridge to dispense a dose of the drug from the cartridge upon movement of the bung with respect to the cartridge,
a drive mechanism comprising a piston rod, the drive mechanism being operable to transfer a driving force to the bung to dispense the dose of the drug from the cartridge, wherein the drug delivery device is configured such that a maximal driving force which is transferrable to the bung via the drive mechanism varies and is adjusted to a current position of the bung within the cartridge, and
an energy storage member adapted to store energy which, when released, provides at least a fraction of the driving force or the whole driving force, wherein the bung is displaceable with respect to the cartridge from an initial position via an intermediate position, in which the cartridge is partly emptied, to an end position, and wherein the maximal driving force is greater when the bung is in the initial position or between the initial position and the intermediate position than when the bung is in the intermediate position or between the intermediate position and the end position,
wherein the piston rod is configured to transfer the driving force to the bung and wherein the piston rod comprises a thread, the thread having a variable pitch or a variable lead, wherein the thread has a distal section facing a distal end of the piston rod and a proximal section being arranged farther away from the distal end of the piston rod than the distal section, wherein in the distal section the pitch of the thread or the lead of the thread is less than the pitch of the thread or the lead of the thread in the proximal section.

2. The drug delivery device of claim 1, wherein the maximal driving force varies between two subsequent doses, the maximal driving force being greater for a first dose which is dispensed from the cartridge than for any subsequent dose which is dispensed from the cartridge.

3. The drug delivery device of claim 1, wherein the drug delivery device is an automatic dispensing device where no user exerted force is transferred to the bung to dispense drug from the cartridge.

4. The drug delivery device of claim 1, comprising a dose setting member which is operable by a user to set the dose, energy being stored within the energy storage member by the user when operating the dose setting member to set the dose.

5. The drug delivery device of claim 1, wherein, when the bung is in the initial position and all of the drug is still within the cartridge, the maximal driving force is greater than a first stiction force which has to be overcome to move the bung with respect to the cartridge, and wherein when the bung is in the intermediate position, the maximal driving force is less than the first stiction force but greater than a second stiction force of the bung in the intermediate position.

6. The drug delivery device of claim 5, wherein the maximal force transferrable to the bung in the intermediate position and originating from energy released from the energy storage member is only a fraction of a driving force required to move the bung from the initial position towards the intermediate position.

7. The drug delivery device of claim 1, wherein the drug delivery device comprises a supplemental storage member within which supplemental energy is stored, the supplemental energy being provided to, when released, provide energy for a supplemental force in order to move the bung from the initial position towards the intermediate position.

8. The drug delivery device of claim 7, wherein the energy stored in the supplemental storage member is less than the energy required to move the bung away from the initial position.

9. The drug delivery device of claim 7, wherein the supplemental storage member biases the piston rod away from an initial position of the piston rod or wherein the supplemental storage member is arranged between the piston rod and the bung.

10. The drug delivery device of claim 1, wherein the piston rod is mechanically decoupled from the bung in the initial position of the piston rod.

11. The drug delivery device of claim 1, wherein the piston rod is coupled to the housing via a first threaded interface and to a further component of the drug delivery device via a second threaded interface, the first and second threaded interfaces having different pitches or leads.

12. The drug delivery device of claim 1, wherein the housing comprises a housing thread to cooperate with the thread of the piston rod and wherein the housing thread comprises a first section and a second section, wherein the first section is adapted to cooperate with the distal section of the thread of the piston rod and wherein the second section is adapted to cooperate with the proximal section of the piston rod.

13. A drug delivery device, comprising:
a housing,
a cartridge containing a drug in a quantity sufficient for a plurality of doses of the drug,
a bung movably retained within the cartridge to dispense a dose of the drug from the cartridge upon movement of the bung with respect to the cartridge,
a drive mechanism operable to transfer a driving force to the bung to dispense the dose of the drug from the cartridge, wherein the drug delivery device is configured such that a maximal driving force which is transferrable to the bung via the drive mechanism varies and is adjusted to a current position of the bung within the cartridge,
an energy storage member adapted to store energy which, when released, provides at least a fraction of the driving force or the whole driving force, wherein the bung is displaceable with respect to the cartridge from an initial position via an intermediate position, in which the cartridge is partly emptied, to an end position, and wherein the maximal driving force is greater when the bung is in the initial position or between the initial position and the intermediate position than when the bung is in the intermediate position or between the intermediate position and the end position,
a supplemental storage member within which supplemental energy is stored, the supplemental energy being provided to, when released, provide energy for a supplemental force in order to move the bung from the initial position towards the intermediate position.

* * * * *